(12) United States Patent
Vasavada et al.

(10) Patent No.: US 9,333,239 B2
(45) Date of Patent: May 10, 2016

(54) USE OF OSTEOPROTEGERIN (OPG) TO INCREASE HUMAN PANCREATIC BETA CELL SURVIVAL AND PROLIFERATION

(71) Applicant: University of Pittsburgh—Of the Commonwealth System of Higher Education, Pittsburgh, PA (US)

(72) Inventors: Rupangi Vasavada, New York, NY (US); Nagesha Guthalu Kondegowda, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 244 days.

(21) Appl. No.: 13/802,159

(22) Filed: Mar. 13, 2013

(65) Prior Publication Data

US 2013/0251668 A1    Sep. 26, 2013

Related U.S. Application Data

(60) Provisional application No. 61/613,356, filed on Mar. 20, 2012.

(51) Int. Cl.
| | |
|---|---|
| *A61K 38/18* | (2006.01) |
| *C07K 14/51* | (2006.01) |
| *C07K 19/00* | (2006.01) |
| *C12N 5/00* | (2006.01) |
| *C12Q 1/02* | (2006.01) |
| *A61K 38/19* | (2006.01) |
| *A61K 45/06* | (2006.01) |
| *A61K 38/28* | (2006.01) |

(52) U.S. Cl.
CPC .............. *A61K 38/191* (2013.01); *A61K 38/28* (2013.01); *A61K 45/06* (2013.01)

(58) Field of Classification Search
None
See application file for complete search history.

(56) References Cited

U.S. PATENT DOCUMENTS

2006/0189528 A1*  8/2006  Roberts ............ C07K 14/70578
530/350

OTHER PUBLICATIONS

Xiang et al. Changes of osteoprotegerin before and after insulin therapy in type diabetic patients, Zhonghua Yixue Zazhi {Beijing, China} ABSTRACT, vol. 87/18:1234-1237 (2007).*
Candido et al. Systemic osteoprotegerin delivery induces pancreatic islet structural and functional alterations in non-diabetic mice, Diabetologia, ABSTRACT, vol. 52, No. S1, pp. S153. Abstract No. 368. Meeting Info: 45th EASD Annual Meeting of the European Association for the Study of Diabetes. Vienna, Austria. (Sep. 30, 2009-Oct. 2, 2009).*

Freshney, Ian. Culture of Animal Cells, A Manual of Basic Technique, Alan R. Liss, Inc., New York, p. 4 (1983).*
Bosco et al., "Unique Arrangement of α- and β-Cells in Human Islets of Langerhans," *Diabetes* 59: 1202-1210 (May 2010).
Braun et al., "Exocytotic Properties of Human Pancreatic β-cells," Mechanisms of Exocytosis: *Ann. N.Y. Acad. Sci.* 1152: 187-193 (2009).
Cabrera et al., "The Unique Cytoarchitecture of Human Pancreatic Islets Has Implications for Islet Cell Function," *PNAS* 103(7): 2334-2339 (Feb. 14, 2006).
Cozar-Castellano et al., "Molecular Control of Cell Cycle Progression in the Pancreatic β-Cell," *Endocrine Reviews* 27: 356-370 (2006).
De Vos et al., "Human and Rat Beta Cells Differ in Glucose Transporter but Not in Glucokinase Gene Expression," *J. Clin. Invest.* 96: 2489-2495 (Nov. 1995).
Fiaschi-Taesch et al., "Survey of the Human Pancreatic β-Cell G1/S Proteome Reveals a Potential Therapeutic Role for Cdk-6 and Cyclin D1 in Enhancing Human β-Cell Replication and Function in Vivo," *Diabetes* 58:882-893 (2009).
Genevay et al., "Beta Cell Adaptation in Pregnancy: A Major Difference Between Humans and Rodents?," *Diabetologia* 53:2089-2092 (2010).
Gunasekaran and Gannon, "Type 2 Diabetes and the Aging Pancreatic Beta Cell," *Aging* 3(6): 565-575 (Jun. 2011).
Kondegowda et al., "[P1-472] Lactogens in the Pathophysiology of Type II Diabetes: Protection Against Glucolipotoxicity (GLT)-Induced β-Cell Death Is Mediated through JAK2/STAT5 Signaling and BclXL," *Pancreatic Islet Biology* (Jun. 19, 2010)(Abstract).
Kondegowda et al., "Osteoprotegerin, a Novel Downstream Target of Lactogens, Directly Enhances Human Beta-Cell Survival and Proliferation," *Endocr. Rev.* 32 (03_MeetingAbstracts): P2-488 (2011)(Abstract).
Levine and Itkin-Ansari, "β-cell Regeneration: Neogenesis, Replication or Both?," *J. Mol. Med.* 86:247-258 (2008).
Parnaud et al., "Proliferation of Sorted Human and Rat Beta Cells," *Diabetologia* 51:91-100 (2008).
Rieck et al., "The Transcriptional Response of the Islet to Pregnancy in Mice," *Molecular Endocrinology* 23: 1702-1712 (2009).
Schrader et al., "Cytokine-Induced Osteoprotegerin Expression Protects Pancreatic Beta Cells Through p38 Mitogen-Activated Protein Kinase Signalling Against Cell Death," *Diabetologia* 50: 1243-1247 (2007).
Serre-Beinier et al., "Cx36 Makes Channels Coupling Human Pancreatic β-Cells, and Correlates with Insulin Expression," *Human Molecular Genetics* 18(3): 428-439 (2009).
Steiner et al., "Pancreatic Islet Plasticity: Interspecies Comparison of Islet Architecture and Composition," *Islets* 2(3): 135-145 (May 2010).
Toffoli et al., "Osteoprotegerin Induces Morphological and Functional Alterations in Mouse Pancreatic Islets," *Molecular and Cellular Endocrinology* 331: 136-142 (2011).

* cited by examiner

*Primary Examiner* — Elizabeth C Kemmerer
*Assistant Examiner* — Regina M Deberry
(74) *Attorney, Agent, or Firm* — Klarquist Sparkman, LLP

(57) ABSTRACT

It is disclosed herein that osteoprotegerin increases human beta cell proliferation and survival. Methods are provided for increasing beta cell proliferation, but contacting a beta cell with an effective amount of osteoprotegrin, a functional fragment, variant or fusion protein thereof. Methods are also provided for treating a human subject with diabetes, comprising administering to the subject a therapeutically effective amount of osteoprotegerin, functional variant or fusion protein thereof.

21 Claims, 10 Drawing Sheets
(6 of 10 Drawing Sheet(s) Filed in Color)

RNA
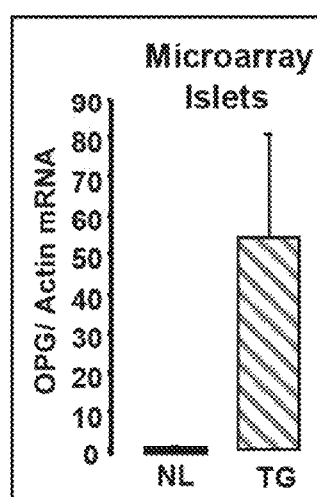
FIG. 2A
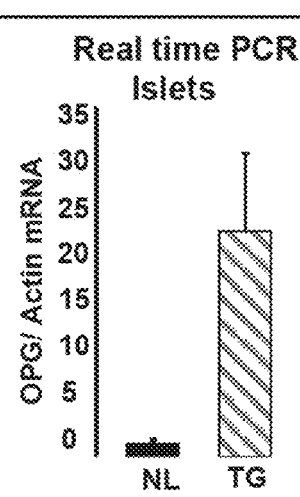
FIG. 2B
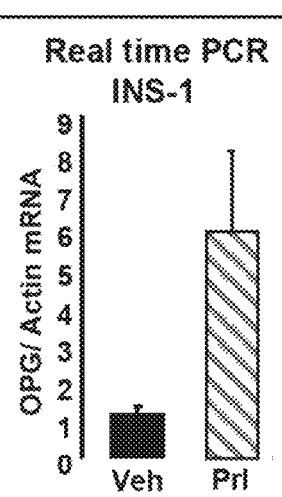
FIG. 2C
Protein
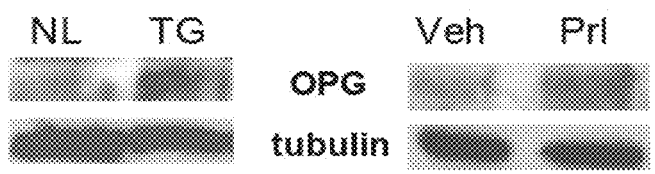
FIG. 2D
FIG. 2E (N=3-8)

USE OF OSTEOPROTEGERIN (OPG) TO INCREASE HUMAN PANCREATIC BETA CELL SURVIVAL AND PROLIFERATION

PRIORITY CLAIM

This claims the benefit of U.S. Application No. 61/613,356, filed Mar. 20, 2012, which is incorporated herein by reference.

STATEMENT OF GOVERNMENT SUPPORT

This invention was made with government support under Grant No. DK072264 awarded by the National Institutes of Health. The government has certain rights in the invention.

FIELD

This relates to the field of diabetes, specifically to methods for increasing human beta cell survival and proliferation.

BACKGROUND

A mammalian pancreas is composed of two subclasses of tissue: the exocrine cells of the acinar tissue and the endocrine cells of the islets of Langerhans. The exocrine cells produce digestive enzymes that are secreted through the pancreatic duct to the intestine. The islet cells produce polypeptide hormones that are involved in carbohydrate metabolism. The islands of endocrine tissue that exist within the adult mammalian pancreas are termed the islets of Langerhans. Adult mammalian islets are composed of five major cell types, the α, β, δ, PP, and ε cells. These cells are distinguished by their production of glucagon, insulin, somatostatin, pancreatic polypeptide, and ghrelin, respectively.

Diabetes mellitus results from the failure of cells to transport endogenous glucose across their membranes either because of an endogenous deficiency of insulin or an insulin receptor defect. Diabetes type 1 is caused by the destruction of β cells, which results in insufficient levels of endogenous insulin. Diabetes type 2, may initiate as a defect in either the insulin receptor itself or in the number of insulin receptors present or in the balance between insulin and glucagon signals, although it is ultimately caused due to a loss of functional β cells. Current treatment of individuals with clinical manifestation of diabetes attempts to emulate the role of the pancreatic β cells in a non-diabetic individual. Individuals with normal β cell function exhibit precise regulation of insulin secretion in response to serum glucose levels. This regulation is due to a feedback mechanism that resides in the β cells that ordinarily prevents surges of blood sugar outside of the normal limits. Unless blood sugar is controlled properly, dangerous or even fatal levels can result. Hence, treatment of a diabetic individual involves monitoring of blood glucose levels and the use of injected bovine, porcine, or cloned human insulin as required. Despite such intervention, there is often a gradual decline in the health of diabetics. Diabetes afflicts millions of people in the United States alone, and there is a clear need to provide additional treatments for this disease.

SUMMARY

It is disclosed herein that osteoprotegerin (OPG) increases beta cell proliferation and survival, specifically human beta cell proliferation and survival. Methods are provided for increasing beta cell proliferation, by contacting a beta cell with an effective amount of OPG, a functional fragment or variant thereof, or a fusion protein thereof, such as an Fc fusion protein.

In some embodiments, methods are provided for treating a subject with diabetes or pre-diabetes, comprising administering to the subject a therapeutically effective amount of OPG, or a functional fragment or a variant thereof, or an Fc Fusion protein thereof. In other embodiments, methods are provided for treating a subject with diabetes or pre-diabetes, comprising administering to the subject a therapeutically effective amount of a nucleic acid encoding OPG, or a functional fragment thereof, a variant thereof, or an Fc Fusion protein thereof. In some embodiments, the subject is human. In yet other embodiments, the subject has type 1 diabetes.

The foregoing and other features and advantages will become more apparent from the following detailed description of several embodiments, which proceeds with reference to the accompanying figures.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 2A-2E shows lactogens regulate OPG. Ratio of OPG/actin (internal control) mRNA in islets from normal (NL) and RIP-mPL1 transgenic (TG) mice cultured in serum-free medium at 5.5 mM glucose for 24 hours (h) (n=4-5 each) by (FIG. 2A) apoptosis PCR array from SABiosciences, and (FIG. 2B) real-time PCR. (FIG. 2C) Prl (200 ng/ml) treatment for 24 h increases OPG/actin mRNA ratio compared to vehicle (veh) treated INS-1 cells by real-time PCR (n=6). (FIG. 2D, FIG. 2E) Preliminary western blot analysis of OPG and tubulin expression in NL and RIP-mPL1 TG mouse islets (FIG. 2D), or INS-1 cells treated±Prl for 24 h (FIG. 2E) (n=2).

FIG. 3A shows the molecular partners of OPG. These graphs show expression of the mRNA encoding receptors RANK and Death Receptor (DR) in mouse islets and INS-1 cells with and without lactogens by real time PCR.

FIG. 4A is a digital image of an immunohistochemical stain showing BrdU (red) and Insulin (green). The 50 ng dose of OPG resulted in a significant increase in β-cell proliferation (n=3 each) in mice. FIG. 4B shows the effect of dose on proliferation in a 7-day study. FIG. 4C shows the effect of dose on β cell proliferation in a 30 day study. Veh=vehicle control.

FIG. 5A shows co-staining of human islet cell cultures (BrdU (red), insulin (green) and DAPI (blue)). FIG. 5B is a bar graph showing the effect of different doses of human osteoprotegerin (hOPG) or vehicle (veh) on β-cell replication in human islet cell cultures treated for 24 h. Quantification of the percentage of BrdU-positive β-cells in the different conditions shows that the 50, 100 and 200 ng/ml doses of hOPG significantly increased β-cell proliferation versus veh-treated cells (n=4-8 preps each in duplicate/triplicate; * p<0.05). FIG. 5C is a bar graph showing that OPG at 100 ng increased β cell proliferation when evaluated using Ki67.

(FIG. 6B) Quantification of TUNEL-positive β-cells in control (Ctrl) and GLT conditions, relative to Veh-Ctrl β-cell death as 100. GLT caused a marked increase in β-cell death in veh-treated cells which was significantly reduced with OPG treatment (n=4 preps, in duplicate). (FIG. 6C) Quantification of TUNEL-positive β-cells in control (Ctrl) and cytokine-treated cells, depicted as fold-over Veh-Ctrl. Cytokines (interleukin (IL)-1β, tumor necrosis factor (TNF)-α, and interferon (IFN)-γ) caused a marked increase in β-cell death in veh-treated cells which was significantly reduced with different doses of hOPG treatment (n=5; 3 human islet preps, in singlicate/duplicate)* p<0.05 vs veh-ctrl; # p<0.05 vs veh-cytokines.

SEQUENCE LISTING

Figure 1:
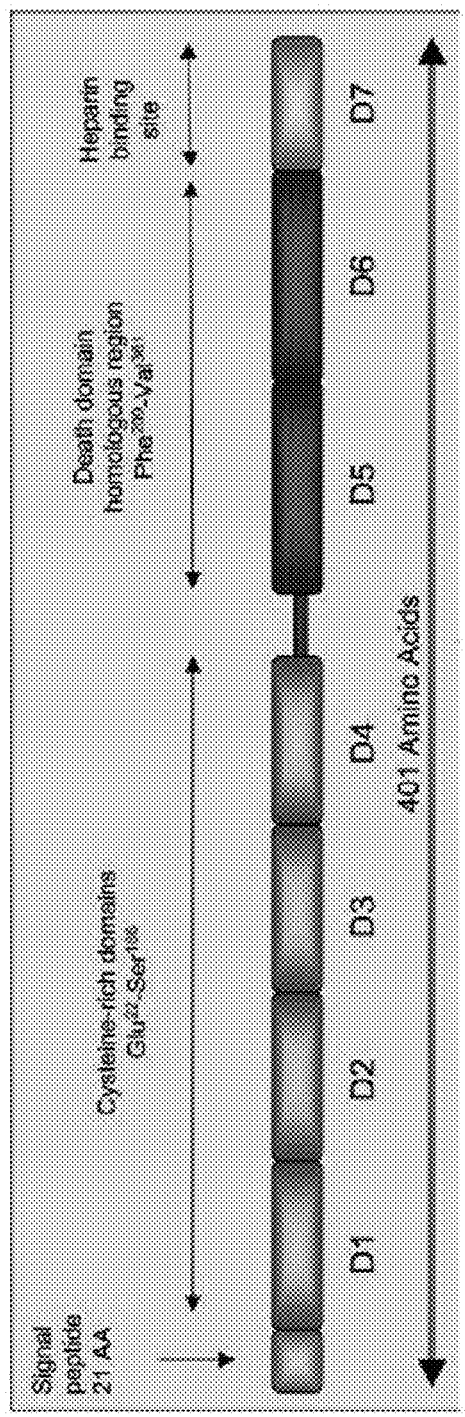
FIG. 1 is a schematic diagram of OPG. (adapted from Holen I, Shipman C M. Role of osteoprotegerin (OPG) in cancer. Clin Sci (Lond). 110:279-291, 2006).

The Sequence Listing is submitted as an ASCII text file [8123-88743-02Sequence_Listing.txt, Mar. 13, 2013, 5.63 KB], which is incorporated by reference herein.

The nucleic and amino acid sequences are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

SEQ ID NO: 1 is the amino acid sequence of human osteoprotogerin.

SEQ ID NO: 2 is an exemplary nucleic acid sequence encoding human osteoprotogerin.

DETAILED DESCRIPTION

Diabetes results from a reduction in the endogenous functional β-cell mass. It is now known that despite this loss, residual β-cells are preserved in the pancreas of patients with diabetes, including people with long-term diabetes. Therefore, an approach to the treatment and cure of both Type 1 and Type 2 diabetes has been to find ways to expand the remnant β-cell mass, such as by increasing β cell proliferation. Recent studies in rodents have shown irrefutably that adult β-cells retain the capacity to regenerate through proliferation. Accumulating evidence suggests that even in humans the β-cell maintains its proliferative capacity. However, the normal rate at which human adult β-cells replicate is very slow. Therefore, one of the top priorities in the treatment of diabetes is to identify agents that have the potential to enhance human β-cell regeneration in vivo.

It is documented herein that OPG can stimulate endogenous β-cell replication in rodents in vivo, and more importantly, human β-cell proliferation in vitro. The studies disclosed herein clearly show that OPG can induce human β-cell proliferation. Besides its proliferative effects, OPG also has pro-survival effects on the β-cell. OPG has the potential to expand, regenerate, and preserve endogenous human functional β-cell mass in vivo under basal and stress-induced conditions and has the capacity to induce proliferation, survival and function in human β-cells.

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

α cells: Mature glucagon producing cells. In vivo, these cells are found in the pancreatic islets of Langerhans.

β cells: Mature insulin producing cells. In vivo, these cells are found in the pancreatic islets of Langerhans, δ cells: Mature somatostatin producing cells. In vivo, these cells are found in the pancreatic islets of Langerhans.

PP cells: Mature pancreatic polypeptide (PP) producing cells. In vivo, these cells are found in the pancreatic islets of Langerhans.

ε cells: Mature ghrelin producing cells. In vivo, these cells are found in the pancreatic islets of Langerhans.

Administration: To provide or give a subject an agent by any effective route. Exemplary routes of administration include, but are not limited to, oral, injection (such as subcutaneous, intramuscular, intradermal, intraperitoneal, intravenous, and intratumoral), sublingual, rectal, transdermal, intranasal, vaginal and inhalation routes.

Agent: Any polypeptide, compound, small molecule, organic compound, salt, polynucleotide, or other molecule of interest. Agent can include a therapeutic agent, a diagnostic agent or a pharmaceutical agent. A therapeutic agent is a substance that demonstrates some therapeutic effect by restoring or maintaining health, such as by alleviating the symptoms associated with a disease or physiological disorder, or delaying (including preventing) progression or onset of a disease.

Amplification: Of a nucleic acid molecule (such as, a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals. Similarly, the term "subject" includes both human and veterinary subjects.

Anti-diabetic lifestyle modifications: Changes to lifestyle, habits, and practices intended to alleviate the symptoms of diabetes or pre-diabetes. Obesity and sedentary lifestyle may both independently increase the risk of a subject developing type II diabetes, so anti-diabetic lifestyle modifications include those changes that will lead to a reduction in a subject's body mass index (BMI), increase physical activity, or both. Specific, non-limiting examples include the lifestyle interventions described in *Diabetes Care*, 22(4):623-34 at pages 626-27, herein incorporated by reference.

Artificial Islets: Clusters of pancreatic endocrine cells formed by the differentiation of stem or progenitor cells including ES cell in vitro, dislodged clusters of pancreatic endocrine cells, endocrine cells differentiated from stem cells or progenitor cells including ES cells in vitro, cells that have undergone a mesenchymal-to-epithelial or epithelial-to-mesenchymal-to-epithelial transition or endocrine cells aggregated into a cluster in vitro.

Diabetes mellitus: A group of metabolic diseases in which a subject has high blood sugar, either because the pancreas does not produce enough insulin, or because cells do not respond to the insulin that is produced. Type 1 diabetes results from the body's failure to produce insulin. This form has also been called "insulin-dependent diabetes mellitus" (IDDM) or "juvenile diabetes". Type 1 diabetes mellitus is characterized by loss of the insulin-producing βcells, leading to insulin deficiency. This type can be further classified as immune-mediated or idiopathic. Type 2 diabetes results from insulin resistance, a condition in which cells fail to use insulin properly, sometimes combined with an absolute insulin deficiency. This form is also called "non insulin-dependent diabetes mellitus" (NIDDM) or "adult-onset diabetes." The defective responsiveness of body tissues to insulin is believed to involve the insulin receptor. Diabetes mellitus is characterized by recurrent or persistent hyperglycemia, and is diagnosed by demonstrating any one of:

a. Fasting plasma glucose level ≥7.0 mmol/l (126 mg/dl);
 b. Plasma glucose ≥11.1 mmol/l (200 mg/dL) two hours after a 75 g oral glucose load as in a glucose tolerance test;
 c. Symptoms of hyperglycemia and casual plasma glucose ≥11.1 mmol/l (200 mg/dl);
 d. Glycated hemoglobin (Hb A1C)≥6.5%

Differentiation: The process whereby relatively unspecialized cells (e.g., embryonic cells) acquire specialized structural and/or functional features characteristic of mature cells. Similarly, "differentiate" refers to this process. Typically, during differentiation, cellular structure alters and tissue-specific proteins appear. The term "differentiated pancreatic endocrine cell" refers to cells expressing a protein characteristic of the specific pancreatic endocrine cell type. A differentiated pancreatic endocrine cell includes an α cell, a β cell, a δ cell, and a PP cell, which express glucagon, insulin, somatostatin, and pancreatic polypeptide, respectively.

Growth factor: A substance that promotes cell growth, survival, and/or differentiation. Growth factors include molecules that function as growth stimulators (mitogens), molecules that function as growth inhibitors (e.g. negative growth factors) factors that stimulate cell migration, factors that function as chemotactic agents or inhibit cell migration or invasion of tumor cells, factors that modulate differentiated functions of cells, factors involved in apoptosis, or factors that promote survival of cells without influencing growth and differentiation. Examples of growth factors are fibroblast growth factor (FGF)2, epidermal growth factor (EGF), ciliary neurotrophic factor (CNTF), hepatocyte growth factor (HGF), nerve growth factor (NGF), and actvin-A.

Effective amount or Therapeutically effective amount: The amount of agent, such as OPG, a functional fragment or variant thereof, that is an amount sufficient to prevent, treat (including prophylaxis), reduce and/or ameliorate the symptoms and/or underlying causes of any of a disorder or disease. In one embodiment, an "effective amount" is sufficient to reduce or eliminate a symptom of a disease, such as a pancreatic cancer. In another embodiment, an effective amount is an amount sufficient to overcome the disease itself.

Endocrine: Tissue which secretes regulatory hormones directly into the bloodstream without the need for an associated duct system.

Expand: A process by which the number or amount of cells in a cell culture is increased due to cell division. Similarly, the terms "expansion" or "expanded" refers to this process. The terms "proliferate," "proliferation" or "proliferated" may be used interchangeably with the words "expand," "expansion," or "expanded." Typically, during an expansion phase, the cells do not differentiate to form mature cells.

Expressed: Translation of a nucleic acid into a protein. Proteins may be expressed and remain intracellular, become a component of the cell surface membrane, or be secreted into the extracellular matrix or medium.

Exocrine: Secretory tissue which distributes its products, such as enzymes, via an associated duct network. The exocrine pancreas is the part of the pancreas that secretes enzymes required for digestion. The exocrine cells of the pancreas include the centroacinar cells and basophilic cells, which produce secretin and cholecystokinin.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used.

Promoters produced by recombinant DNA or synthetic techniques may also be used to provide for transcription of the nucleic acid sequences.

Heterologous: A heterologous sequence is a sequence that is not normally (in the wild-type sequence) found adjacent to a second sequence. In one embodiment, the sequence is from a different genetic source, such as a virus or organism, than the second sequence.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Islets of Langerhans: Small discrete clusters of pancreatic endocrine tissue. In vivo, in an adult mammal, the islets of Langerhans are found in the pancreas as discrete clusters (islands) of pancreatic endocrine tissue surrounded by the pancreatic exocrine (or acinar) tissue. In vivo, the islets of Langerhans consist of the α cells, β cells, δ cells, PP cells, and ε cells. Histologically, in rodents, the islets of Langerhans consist of a central core of β cells surrounded by an outer layer of α cells, δ cells, and PP cells. The structure of human islets of Langerhans is different and distinct from rodents. The islets of Langerhans are sometimes referred to herein as "islets."

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids. An isolated cell type has been substantially separated from other cell types, such as a different cell type that occurs in an organ. A purified cell or component can be at least 90%, at least 95%, at least 96%, at least 97%, at least 98%, or at least 99% pure.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes.

Mammal: This term includes both human and non-human mammals. Similarly, the term "subject" includes both human and veterinary subjects.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, such as a "recombinant polypeptide." A recombinant nucleic acid may serve a non-coding function (such as a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see for example, *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, such as version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (http://www.ncbi.nlm.nih.gov/). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989).

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

ORF (open reading frame): A series of nucleotide triplets (codons) coding for amino acids without any termination codons. These sequences are usually translatable into a peptide.

Osteoprotegerin (OPG): A protein of the Tumor Necrosis Factor (TNF) receptor family, also known as osteoclastogenesis inhibitory factor (OCIF), or tumor necrosis factor receptor superfamily member 11B (TNFRSF11B), was first described by Simonet et al. (Cell, 89, 309-319 (1997)). OPG appears to be a crucial element in regulating the natural processes of bone production and turnover. Changes in the balance between OPG and its target receptor activator of nuclear factor kappa B ligand (RANKL) have been noted in a number of conditions associated with abnormal bone metabolism. OPG has undergone preclinical and clinical testing for conditions associated with increased bone turnover and bone loss, including osteoporosis, rheumatoid arthritis, Paget's disease, periodontal disease, vascular disease and cancers that are located in or have metastasized to bone (For review, see Lorenz et al., J. Amer Med Assoc 292: 490-5 (2004)). OPG is disclosed in U.S. Pat. Nos. 6,015,938, 6,284,740, 6,284,728, 6,613,544, 6,316,408, 6,288,032 and 6,369,027, which are incorporated herein by reference.

Pancreatic endocrine cell: An endocrine cell of pancreatic origin that produces one or more pancreatic hormone, such as insulin, glucagon, somatostatin, or pancreatic polypeptide. Subsets of pancreatic endocrine cells include the α (glucagon producing), β (insulin producing) δ (somatostatin producing) or PP (pancreatic polypeptide producing) cells. Additional subsets produce more than one pancreatic hormone, such as, but not limited to, a cell that produces both insulin and glucagon, or a cell that produces insulin, glucagon, and somatostatin, or a cell that produces insulin and somatostatin.

Pancreatic cancer: A malignant tumor within the pancreas. The prognosis is generally poor. About 95% of pancreatic cancers are adenocarcinomas. The remaining 5% are tumors of the exocrine pancreas (for example, serous cystadenomas), acinar cell cancers, and pancreatic neuroendocrine tumors (such as insulinomas). An "insulinoma" is a cancer of the beta cells that retains the ability to secrete insulin. Patients with insulinomas usually develop neuroglycopenic symptoms. These include recurrent headache, lethargy, diplopia, and blurred vision, particularly with exercise or fasting. Severe hypoglycemia may result in seizures, coma and permanent neurological damage. Symptoms resulting from the catecholaminergic response to hypoglycemia (for example, tremulousness, palpitations, tachycardia, sweating, hunger, anxiety, nausea). A pancreatic adenocarciona occurs in the glandular tissue. Symptoms include abdominal pain, loss of appetite, weight loss, jaundice and painless extension of the gallbladder.

Classical treatment for pancreatic cancer, including adenocarcinomas and insulinomas includes surgical resection (such as the Whipple procedure) and chemotherapy with agent such as fluorouracil, gemcitabine, and erlotinib.

Pre-diabetes: A state in which some, but not all, of the criteria for diabetes are met. For example, a subject can have impaired fasting glycaemia or impaired fasting glucose (IFG). Subjects with fasting glucose levels from 110 to 125 mg/dl (6.1 to 6.9 mmol/l) are considered to have impaired fasting glucose. Subjects with plasma glucose at or above 140 mg/dL (7.8 mmol/L), but not over 200 mg/dL (11.1 mmol/L), two hours after a 75 g oral glucose load are considered to have impaired glucose tolerance.

Predisposition for diabetes: A subject that is at high risk for developing diabetes. A number of risk factors are known to those of skill in the art and include: genetic factors (e.g., carrying alleles that result in a higher occurrence of diabetes than in the average population or having parents or siblings with diabetes); overweight (e.g., body mass index (BMI) greater or equal to 25 kg/m.sup.2); habitual physical inactivity, race/ethnicity (e.g., African-American, Hispanic-American, Native Americans, Asian-Americans, Pacific Islanders); previously identified impaired fasting glucose or impaired glucose tolerance, hypertension (e.g., greater or equal to 140/90 mmHg in adults); HDL cholesterol greater or equal to 35 mg/dl; triglyceride levels greater or equal to 250 mg/dl; a history of gestational diabetes or delivery of a baby over nine pounds; and/or polycystic ovary syndrome. See, e.g., "Report of the Expert Committee on the Diagnosis and Classification of Diabetes Mellitus" and "Screening for Diabetes" Diabetes Care 25(1): S5-S24 (2002).

Polypeptide: A polymer in which the monomers are amino acid residues that are joined together through amide bonds.

When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced.

The term "polypeptide fragment" refers to a portion of a polypeptide which exhibits at least one useful epitope. The term "functional fragments of a polypeptide" refers to all fragments of a polypeptide that retain an activity of the polypeptide. Biologically functional fragments, for example, can vary in size from a polypeptide fragment as small as an epitope capable of binding an antibody molecule to a large polypeptide capable of participating in the characteristic induction or programming of phenotypic changes within a cell. An "epitope" is a region of a polypeptide capable of binding an immunoglobulin generated in response to contact with an antigen. Thus, smaller peptides containing the biological activity of insulin, or conservative variants of the insulin, are thus included as being of use.

The term "soluble" refers to a form of a polypeptide that is not inserted into a cell membrane.

The term "substantially purified polypeptide" as used herein refers to a polypeptide which is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative substitutions replace one amino acid with another amino acid that is similar in size, hydrophobicity, etc. Variations in the cDNA sequence that result in amino acid changes, whether conservative or not, should be minimized in order to preserve the functional and immunologic identity of the encoded protein. The immunologic identity of the protein may be assessed by determining if it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80, 90 or even 95% or 98% identical to the native amino acid sequence.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or a composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

Polynucleotide: A nucleic acid sequence (such as a linear sequence) of any length. Therefore, a polynucleotide includes oligonucleotides, and also gene sequences found in chromosomes. An "oligonucleotide" is a plurality of joined nucleotides joined by native phosphodiester bonds. An oligonucleotide is a polynucleotide of between 6 and 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Primers: Short nucleic acids, for example DNA oligonucleotides 10 nucleotides or more in length, which are annealed to a complementary target DNA strand by nucleic acid hybridization to form a hybrid between the primer and the target DNA strand, then extended along the target DNA strand by a DNA polymerase enzyme. Primer pairs can be used for amplification of a nucleic acid sequence, such as by the polymerase chain reaction (PCR) or other nucleic-acid amplification methods known in the art.

Probes and primers as used in the present invention may, for example, include at least 10 nucleotides of the nucleic acid sequences that are shown to encode specific proteins. In order to enhance specificity, longer probes and primers may also be employed, such as probes and primers that comprise 15, 20, 30, 40, 50, 60, 70, 80, 90 or 100 consecutive nucleotides of the disclosed nucleic acid sequences. Methods for preparing and using probes and primers are described in the references, for example Sambrook et al. (1989) Molecular Cloning: A Laboratory Manual, Cold Spring Harbor, N.Y.; Ausubel et al. (1987) Current Protocols in Molecular Biology, Greene Publ. Assoc. & Wiley-Intersciences; Innis et al. (1990) PCR Protocols, A Guide to Methods and Applications, Innis et al. (Eds.), Academic Press, San Diego, Calif. PCR primer pairs can be derived from a known sequence, for example, by using computer programs intended for that purpose such as Primer (Version 0.5, 1991, Whitehead Institute for Biomedical Research, Cambridge, Mass.).

When referring to a probe or primer, the term "specific" for (a target sequence) indicates that the probe or primer hybridizes under stringent conditions substantially only to the target sequence in a given sample comprising the target sequence.

Promoter: A promoter is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, such as by genetic engineering techniques. Similarly, a recombinant protein is one encoded for by a recombinant nucleic acid molecule.

Sequence identity of amino acid sequences: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, CABIOS 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of OPG are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specific binding agent: An agent that binds substantially only to a defined target. Thus a β cell specific binding agent is an agent that binds substantially to a β cell, and a pancreatic endocrine cell specific binding agent is an gent that binds substantially only to pancreatic endocrine cells or a subset thereof (and not to pancreatic exocrine cells). Similarly, a pancreatic exocrine cell specific binding agent is an agent that binds substantially to exocrine cells. In one embodiment, the specific binding agent is a monoclonal or polyclonal antibody that specifically binds a type of pancreatic cell.

The term "specifically binds" refers, with respect to a cell, such as a pancreatic endocrine cell, to the preferential association of an antibody or other ligand, in whole or part, with a cell or tissue bearing that antigen and not to cells or tissues lacking that antigen. It is, of course, recognized that a certain degree of non-specific interaction may occur between a molecule and a non-target cell or tissue. Nevertheless, specific binding may be distinguished as mediated through specific recognition of the antigen. Although selectively reactive antibodies bind antigen, they may do so with low affinity. On the other hand, specific binding results in a much stronger association between the antibody (or other ligand) and cells bearing the antigen than between the bound antibody (or other ligand) and cells lacking the antigen. Specific binding typically results in greater than 2-fold, such as greater than 5-fold, greater than 10-fold, or greater than 100-fold increase in amount of bound antibody or other ligand (per unit time) to a cell or tissue expressing the target epitope as compared to a cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Subject: Any mammal, such as humans, non-human primates, pigs, sheep, cows, rodents and the like which is to be the recipient of the particular treatment. In two non-limiting examples, a subject is a human subject or a murine subject.

Therapeutic agent: Used in a generic sense, it includes treating agents, prophylactic agents, and replacement agents. A therapeutic agent can be an antibody that specifically binds pancreatic endocrine cells or a subset thereof.

Transduced and Transformed: A virus or vector "transduces" a cell when it transfers nucleic acid into the cell. A cell is "transformed" or "transfected" by a nucleic acid transduced into the cell when the DNA becomes stably replicated by the cell, either by incorporation of the nucleic acid into the cellular genome, or by episomal replication.

Numerous methods of transfection are known to those skilled in the art, such as: chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelope/capsid-DNA complexes) and by biological infection by viruses such as recombinant viruses {Wolff, J. A., ed, Gene Therapeutics, Birkhauser, Boston, USA (1994)}. In the case of infection by retroviruses, the infecting retrovirus particles are absorbed by the target cells, resulting in reverse transcription of the retroviral RNA genome and integration of the resulting provirus into the cellular DNA. Methods for the introduction of genes into the pancreatic endocrine cells are known (e.g. see U.S. Pat. No. 6,110,743, herein incorporated by reference). These methods can be used to transduce a pancreatic endocrine cell produced by the methods described herein, or an artificial islet produced by the methods described herein.

Genetic modification of the target cell is an indicium of successful transfection. "Genetically modified cells" refers to cells whose genotypes have been altered as a result of cellular uptakes of exogenous nucleotide sequence by transfection. A reference to a transfected cell or a genetically modified cell includes both the particular cell into which a vector or polynucleotide is introduced and progeny of that cell.

Transgene: An exogenous gene supplied by a vector.

Vector: A nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Osteoprotegerin (OPG) and Variants Thereof

OPG is a member of the TNF receptor superfamily. Human wild-type OPG has the amino acid sequence set forth as MNKLLCCALV FLDISIKWTT QETFPPKYLH YDEETSHQLL CDKCPPGTYL KQHCTAKWKT VCAPCPDHYY TDSWHTSDEC LYCSPVCKEL QYVKQECNRT HNRVCECKEG RYLEIEFCLK HRSCPPGFGV VQAGTPERNT VCKRCPDGFF SNETSSKAPC RKHTNCSVFG LLLTQKGNAT HDNICSGNSE STQKCGIDVT LCEEAFFRFA VPTKFTPNWL SVLVDNLPGT KVNAESVERI KRQHSSQEQT FQLLKLWKHQ NKAQDIVKKI IQDIDLCENS VQRHIGHANL TFEQLRSLME SLPGKKVGAE DIEKTIKACK PSDQILKLLS LWRIKNGDQD TLKGLMHALK HSKTYHFPKT VTQSLKKTIR FLHSFTMYKL YQKLFLEMIG NQVQSVKISC L (GENBANK® Accession No. AAB53709.1 and NP_002537.3, both incorporated herein by reference, SEQ ID NO: 1).

Wild-type OPG is an atypical member of the TNF receptor superfamily (TNFRS), in that it is a secreted protein with no transmembrane domain and no direct signaling properties. OPG secretion is through a 21-residue signal peptide which is cleaved, generating a mature protein of 380 amino acids. Thus, in some embodiments, the method includes administering an OPG functional fragment including or consisting of amino acids 22-401 of SEQ ID NO: 1. OPG sequences of use encompass those that have the amino terminal leader sequence of 21 amino acids removed and/or where amino acids are removed from the C-terminus up to and including amino acid 185.

OPG has three major structural motifs: i) four cysteine-rich TNF receptor domains which are necessary and sufficient for binding to its target; ii) a heparin-binding domain that is involved in homodimer formation; and iii) two death domain homologous (DDH) regions with unknown functional role (FIG. 1). Wild-type OPG is produced as a monomer (55-62 kDa), but gets dimerized and is secreted as a disulfide-linked homodimeric glycoprotein of 110-120 kDa.

A variant of OPG can be at least 95%, 96%, 97%, 98%, 99% identical to SEQ ID NO: 1, or amino acids 22-410 of SEQ ID NO: 1; these variants are of use in the disclosed methods. In some embodiments, these variants retain the ability to form dimers and interact with RANKL and/or bind TNF-related apoptosis inducing ligand (TRAIL). OPG is a decoy receptor for TRAIL, modulates TRAIL's ability to target cells. Without being bound by theory, OPG is active in bone metabolism, and particular it inhibits bone resorption and increases bone density. The interaction of OPG with RANKL inhibits RANKL's ability to stimulate the formation and activity of osteoclasts via its interaction with RANK, and it is this activity of OPG that confers its ability to reduce bone loss. The biological activities of OPG also include activity associated with binding to TRAIL.

Active functional fragments of OPG can also be used in the methods disclosed herein. Yamaguchi et al. (J. Biol. Chem. 273, 5117-5123, 1998, incorporated herein by reference) demonstrated that truncated and deleted variants of OPG retained OPG-like activity, while OPG in both monomer or dimer form retained biological activity (Tomoyasu, A et al., Biochem Biophys Res Commun 245, 382-387 (1998)). Schneeweis et al., (J. Biol. Chem. Oct. 7, 2005 (epub)) examined the assembly, state and affinity of OPG for RANKL. Dimerization of OPG either in full length form, where the dimerization is mediated by non-covalent interactions within the death domain regions, or in truncated form, such as where dimerization may be mediated by Fc attachment, results in high affinity attachment of OPG to RANKL.

Variants of OPG that retain binding to RANKL are also known, see U.S. Published Patent Application No. 2010/0144600 and U.S. Pat. No. 7,612,169, both incorporated herein by reference. In some embodiments, an OPG variant protein is a modified version of a full length wild type OPG sequence. In another embodiment, the OPG variant protein contains one or more additional insertions or deletions at the N-terminus, C-terminus, or internally. For example, the OPG variant protein may consist of any modified active functional fragment of OPG. The active functional fragment may consist of, for example, amino acids 22-294, amino acids 22-201, 22-194 or amino acids 1-197.

In some embodiments, OPG variant proteins have at least one amino acid residue that differs from a wild-type OPG sequence, such as at most 2, 3, 4, or 5 different residues. The modifications can be amino acid substitutions and may include those to surface or exposed areas of OPG. OPG variant proteins may include one domain or multiple domains connected by linker sequences. OPG variant proteins can contain further modifications, for instance modifications that alter stability or immunogenicity or which enable posttranslational modifications such as PEGylation or glycosylation.

In one embodiment, the OPG variant protein includes at least one modification in the region encompassed by amino acid residues 102-130. For example, the OPG variant protein includes at least one amino acid substitution at positions 102, 111, 115, 122, 128 or 130. In other embodiments, the OPG variant protein includes at least one modification within the loop structure comprising residues 107-118. In another embodiment, the modification in this region includes substitution of Ile at position 115. Ile at position 115 can be substituted by amino acids that are more polar or have shorter side chains. In some examples, Ile at position 115 is substituted with Thr, Met, Val, Asp, Gly. Ser or Arg. Thus, modifications of use include I115T, I115M, I115V, I115D, I115G, I115S and I115R.

In some embodiments, the OPG variant protein comprises at least one modification in the region encompassed by amino acid residues 120-130. In another embodiment, the modification involves substitution of Arg at position 122. In some examples, Arg at position 122 is substituted with Gly, Gln, Ser, Asn or Glu. Thus, modifications include R122G, R122Q, R122S, R122N and R122E. In other examples, the modification involves substitution of Phe at position 128. For example, Phe at position 128 can be substituted with Val, Ala, Leu, Ile or Ser. Thus, modifications include F128V, F128A, F128L, F128 I and F128S. In other examples, the modification involves substitution of Val at position 130. For example, Val at position 130 is substituted with Glu or Ala.

In some embodiments, the OPG variant protein comprises at least two modifications or at most two modifications. The at two modifications can both occur in the region encompassed by residues 102-130. For example, at least two modifications can include substitutions at positions 115 and 122. Examples of suitable double modifications within this region are R122N and I115M; R122N and I115M; F128S and I115M; F128I and I115M; and F128L and I115M. Alternatively, at least two modifications can include one or more modifications within the region encompassed by amino acids 102-130 and one or more modifications outside of this region. The modification outside of this region can occur at, for example, any one or more of residues 31, 40, 51, 100, 155, 167 or 168. In one embodiment, the residue 40 is modified. In some embodiments, Leu at position 40 is substitute with Ser.

In another embodiment, the OPG variant protein of use in the present methods comprises one or more modifications within the region encompassed by amino acids 102-130 and a modification to any one or more of the following amino acid residues: Gln21, Glu22, Thr23, Phe24, Pro25, Pro26, Lys27, Tyr28, Leu29, His30, Tyr31, Asp32, Glu33, Glu34, Thr35, Ser36, His37, Gln38, Asp42, Lys43, Pro45, Pro46, Thr48, Lys51, Gln52, His53, Cys54, Thr55, Ala56, Lys57, Trp58, Lys59, Thr60, Val61, Ala63, Pro64, Pro66, Asp67, His68, Tyr69, Asp72, Ser73, Trp74, Thr76, Ser77, Asp78, Glu79, Leu81, Tyr82, Ser84, Pro85, Val86, Lys88, Glu89, Leu90, Tyr92, Val93, Lys94, Gln95, Glu96, Asn98, Arg99, Thr100, His101, Val131, Gln132, Ala133, Gly134, Thr135, Pro136, Glu137, Arg138, Val141, Lys143, Arg144, Cys145, Pro146, Asp147, Gly148, Phe149, Phe150, Ser151, Asn152, Glu153, Thr154, Ser155, Ser156, Lys157, Ala158, Pro159, Cys160, Arg161, Lys162, His163, Thr164, Asn165, Cys166, Ser167, Val168, Phe169, Gly170, Leu171, Leu172, Leu173, Thr174, Gln175, Lys176, Gly177, Asn178, Ala179, Thr180, His181, Asp182, Asn183, Ile184, Cys185, Ser186, Gly187, Asn188, Ser189, Glu190, Ser191, Thr192, Gln193, Lys194, Cys195, Gly196, Ile197, Asp198, Val199, Thr200 and Leu201. In other embodiments the OPG variant protein of use in the present methods includes one or more modifications within the region encompassed by amino acids 102-130 and a modification to any one or more of the following amino acid residues: Tyr28, His30, Tyr31, Glu34, Thr35, Ser36, His 37, Lys43, Tyr49, Gln52, His53, Pro66, Asp67, His68, Tyr69, Tyr70, Thr71, Asp72, Ser73, Trp74, His75, Thr76, Ser77, Asp78, Glu79, Cys80, Leu81, Tyr82, Cys83, Ser84, Pro85, Val86, Cys87, Lys88, Glu89, Leu90, Gln91, Asn139 and Glu153. Additional variants of OPG of use are disclosed in U.S. Published Patent Application No. 2010/0144600, which is incorporated herein by reference.

OPG can be included in a fusion protein. Thus, in some embodiments, the OPG is administered as a fusion protein, such as an Fc fusion protein. In some specific, non-liming examples, the Fc domain is an IgG Fc domain, such as an $IgG_1$, $IgG_2$, $IgG_3$ or an $IgG_4$ Fc domain. In some embodiments, these forms of OPG have an increased half-life as compared to the OPG not included in the fusion protein. Exemplary fusion proteins are commercially available, such as Human Osteoprotegerin/TNFRSF11B Fc Chimera from R and D Systems, Catalog Number: 805-OS and Mouse Osteoprotegerin/TNFRSF11B Fc Chimera from R and D Systens, Catalog Number 459-MO.

Without being bound by theory, the Fc domain increases the half-life of an

IgG through its unique pH-dependent association with the neonatal Fc receptor (FcRn). After internalization, the Fc domain of IgG can bind to FcRn in the acidic environment of the endosome, so that the IgG is then cycled onto the cell surface and re-released into circulation. This biological system protects IgG from degradation and results in a long serum half-life. Fusions of an Fc domain and a therapeutic molecule have an extended half life. In addition, since the Fc fragment of IgG consists of a tightly packed homodimer, two therapeutic proteins are present in each molecule. Recently, monomeric Fc fusion proteins were generated in which a single active protein was fused to dimeric wild-type Fc. These smaller molecules have been shown to possess even extended half-lives compared with the dimeric version.

Polynucleotides and Vectors

Polynucleotide molecules encoding OPG, a functional fragment, variant, or fusion protein thereof can readily be produced by one of skill in the art, using the amino acid sequences provided herein, and the genetic code. In addition, one of skill can readily construct a variety of clones containing functionally equivalent nucleic acids, such as nucleic acids which differ in sequence but which encode protein sequence. An Exemplary nucleic acid sequence encoding human OPG is provided below.

```
                                              (SEQ ID NO: 2)
GTATATATAA CGTGATGAGC GTACGGGTGC GGAGACGCAC

CGGAGCGCTC GCCCAGCCGC CGYCTCCAAG CCCCTGAGGT

TTCCGGGGAC CACAATGAAC AAGTTGCTGT GCTGCGCGCT

GACATCTCCA TTAAGTGGAC CACCCAGGAA ACGTTTCCTC

CAAAGTACCT TCATTATGAC GAAGAAACCT CTCATCAGCT

GTTGTGTGAC AAATGTCCTC CTGGTACCTA CCTAAAACAA

CACTGTACAG CAAAGTGGAA GACCGTGTGC GCCCCTTGCC

CTGACCACTA CTACACAGAC AGCTGGCACA CCAGTGACGA

GTGTCTATAC TGCAGCCCCG TGTGCAAGGA GCTGCAGTAC

GTCAAGCAGG AGTGCAATCG CACCCACAAC CGCGTGTGCG
```

```
AATGCAAGGA AGGGCGCTAC CTTGAGATAG AGTTCTGCTT

GAAACATAGG AGCTGCCCTC CTGGATTTGG AGTGGTGCAA

GCTGGAACCC CAGAGCGAAA TACAGTTTGC AAAAGATGTC

CAGATGGGTT CTTCTCAAAT GAGACGTCAT CTAAAGCACC

CTGTAGAAAA CACACAAATT GCAGTGTCTT TGGTCTCCTG

CTAACTCAGA AAGGAAATGC AACACACGAC AACATATGTT

CCGGAAACAG TGAATCAACT CAAAAATGTG GAATAGATGT

TACCCTGTGT GAGGAGGCAT TCTTCAGGTT TGCTGTTCCT

ACAAAGTTTA CGCCTAACTG GCTTAGTGTC TTGGTAGACA

ATTTGCCTGG CACCAAAGTA AACGCAGAGA GTGTAGAGAG

GATAAAACGG CAACACAGCT CACAAGAACA GACTTTCCAG

CTGCTGAAGT TATGGAAACA TCAAAACAAA GCCCAAGATA

TAGTCAAGAA GATCATCCAA GATATTGACC TCTGTGAAAA

CAGCGTGCAG CGGCACATTG GACATGCTAA CCTCACCTTC

GAGCAGCTTC GTAGCTTGAT GGAAAGCTTA CCGGGAAAGA

AAGTGGGAGC AGAAGACATT GAAAAAACAA TAAAGGCATG

CAAACCCAGT GACCAGATCC TGAAGCTGCT CAGTTTGTGG

CGAATAAAAA ATGGCGACCA AGACACCTTG AAGGGCCTAA

TGCACGCACT AAAGCACTCA AAGACGTACC ACTTTCCCAA

AACTGTCACT CAGAGTCTAA AGAAGACCAT CAGGTTCCTT

CACAGCTTCA CAATGTACAA ATTGTATCAG AAGTTATTTT

TAGAAATGAT AGGTAACCAG GTCCAATCAG TAAAAATAAG

CTGCTTATAA CTGGAAATGG CCATTGAGCT GTTTCCTCAC

AATTGGCGAG ATCCCATGGA TGATAA
```

Polynucleotides include DNA, cDNA and RNA sequences which encode the peptide of interest. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (see, for example, Stryer, 1988, Biochemistry, 3.sup.rd Edition, W.H. 5 Freeman and Co., NY).

A nucleic acid encoding OPG, variants thereof and fusion proteins can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., Cold Spring Harbor Symp. Quant. Biol. 51:263, 1987; and Erlich, ed., PCR Technology, (Stockton Press, NY, 1989). Polynucleotides also can be isolated by screening genomic or cDNA libraries with probes selected from the sequences of the desired polynucleotide under stringent hybridization conditions.

Nucleic acid sequences encoding OPG, a functional fragment, variant, or fusion protein thereof can be prepared by any suitable method including, for example, cloning of appropriate sequences or by direct chemical synthesis by methods such as the phosphotriester method of Narang et al., Meth. Enzymol. 68:90-99, 1979; the phosphodiester method of Brown et al., Meth. Enzymol. 68:109-151, 1979; the diethylphosphoramidite method of Beaucage et al., Tetra. Lett. 22:1859-1862, 1981; the solid phase phosphoramidite triester method described by Beaucage & Caruthers, Tetra. Letts. 22(20):1859-1862, 1981, for example, using an automated synthesizer as described in, for example, Needham-VanDevanter et al., Nucl. Acids Res. 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids encoding sequences encoding OPG, a functional fragment, variant, or fusion protein thereof can be prepared by cloning techniques. Examples of appropriate cloning and sequencing techniques, and instructions sufficient to direct persons of skill through cloning are found in Sambrook et al., supra, Berger and Kimmel (eds.), supra, and Ausubel, supra. Product information from manufacturers of biological reagents and experimental equipment also provide useful information. Such manufacturers include the SIGMA® Chemical Company (Saint Louis, Mo.), R&D Systems (Minneapolis, Minn.), Pharmacia Amersham (Piscataway, N.J.), CLONTECH® Laboratories, Inc. (Palo Alto, Calif.), Chem Genes Corp., Aldrich Chemical Company (Milwaukee, Wis.), Glen Research, Inc., GIBCO® BRL Life Technologies, Inc. (Gaithersburg, Md.), Fluka Chemica-Biochemika Analytika (Fluka Chemie AG, Buchs, Switzerland), INVITROGEN® (San Diego, Calif.), and Applied Biosystems (Foster City, Calif.), as well as many other commercial sources known to one of skill Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill In one example, OPG, a functional fragment, variant, or fusion protein thereof is prepared by inserting the cDNA which encodes the protein into a vector. The insertion can be made so that the protein and a heterologous protein are read in frame so that one continuous polypeptide is produced.

Once the nucleic acids encoding OPG, a functional fragment, variant, or fusion protein thereof are isolated and cloned, the protein can be expressed in a recombinantly engineered cell such as bacteria, plant, yeast, insect and mammalian cells using a suitable expression vector. One or more DNA sequences OPG, a functional fragment, variant, or fusion protein thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Polynucleotide sequences encoding OPG, a functional fragment, variant, or fusion protein thereof can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding OPG, a functional fragment, variant, or fusion protein thereof can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

In one embodiment, vectors are used for expression in yeast such as *S. cerevisiae* or *Kluyveromyces lactis*. Several promoters are known to be of use in yeast expression systems such as the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, many inducible promoters are of use, such as GAL1-10 (induced by galactose), PHOS (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2μ) or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation. The polynucleotides can also be designed to express in insect cells.

OPG, a functional fragment, variant, or fusion protein thereof can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in a yeast lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

Viral vectors can also be prepared encoding OPG, a functional fragment, variant, or fusion protein thereof. A number of viral vectors have been constructed, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,2217, 879), alphaviruses (S. Schlesinger, 1993, Trends Biotechnol. 11:18-22; I. Frolov et al., 1996, Proc. Natl. Acad. Sci. USA 93:11371-11377) and retroviruses of avian (Brandyopadhyay et al., 1984, Mol. Cell Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell Biol., 5:431-437; Sorge et al., 1984, Mol. Cell Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.). Thus, in one embodiment, the polynucleotide encoding OPG, a functional fragment, variant, or fusion protein thereof is included in a viral vector. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like. Pox viruses of use include orthopox, suipox, avipox, and capripox virus. Orthopox include vaccinia, ectromelia, and raccoon pox. One example of an orthopox of use is vaccinia. Avipox includes fowlpox, canary pox and pigeon pox. Capripox include goatpox and sheeppox. In one example, the suipox is swinepox. Examples of pox viral vectors for expression as described for example, in U.S. Pat. No. 6,165,460, which is incorporated herein by reference. Other viral vectors that can be used include other DNA viruses such as herpes virus and adenoviruses, and RNA viruses such as retroviruses and polio.

The vector can encode a selectable marker. In one example, the poxvirus includes, for example, a thymidine kinase gene (see U.S. Pat. No. 6,998,252, which is incorporated herein by reference).

Viral vectors that OPG, a functional fragment, variant, or fusion protein thereof include at least one expression control element operationally linked to the nucleic acid sequence encoding OPG, variants thereof and fusion proteins. The expression control elements are inserted in the vector to control and regulate the expression of the nucleic acid sequence. Examples of expression control elements of use in these vectors includes, but is not limited to, lac system, operator and promoter regions of phage lambda, yeast promoters and promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding OPG, a functional fragment, variant, or fusion protein thereof in the host system. The expression vector can contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecular Biology," John Wiley and Sons, New York, N.Y.) and are commercially available.

Basic techniques for preparing recombinant DNA viruses containing a heterologous DNA sequence encoding OPG, variants thereof and fusion proteins, are known in the art. Such techniques involve, for example, homologous recombination between the viral DNA sequences flanking the DNA sequence in a donor plasmid and homologous sequences present in the parental virus (Mackett et al., 1982, Proc. Natl. Acad. Sci. USA 79:7415-7419. The vector can be constructed for example by steps known in the art, such as by using a unique restriction endonuclease site that is naturally present or artificially inserted in the parental viral vector to insert the heterologous DNA.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, Jakoby and Pastan (eds), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features. As discussed above, techniques for the transformation of yeast cells, such as polyethylene glycol transformation, protoplast transformation and gene guns are also known in the art (see Gietz and Woods Methods in Enzymology 350: 87-96, 2002).

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding OPG, a functional fragment, variant, or fusion protein thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Isolation and purification of recombinantly expressed polypeptide can be carried out by conventional means including preparative chromatography and immunological separations. Once expressed, OPG, a functional fragment, variant, or fusion protein thereof can be purified according to standard procedures of the art, including ammonium sulfate precipitation, affinity columns, column chromatography, and the like (see, generally, R. Scopes, *Protein Purification*, Springer-Verlag, N.Y., 1982). Substantially pure compositions of at least about 90 to 95% homogeneity are disclosed herein, and 98 to 99% or more homogeneity can be used for pharmaceutical purposes. Once purified, partially or to homogeneity as desired, if to be used therapeutically, the polypeptides should be substantially free of endotoxin.

In addition to recombinant methods, OPG, a functional fragment, variant, or fusion protein thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A*. pp. 3-284; Merrifield et al., *J. Am. Chem. Soc.* 85:2149-2156, 1963, and Stewart et al., *Solid Phase Peptide Synthesis, 2nd ed.*, Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art.

Pharmaceutical Compositions and Therapeutic Methods

Pharmaceutical compositions that include OPG, a functional fragment, variant, or fusion protein thereof, or a nucleic acid encoding these polypeptides, can be formulated with an appropriate pharmaceutically acceptable carrier, depending upon the particular mode of administration chosen.

In some embodiments, the pharmaceutical composition consists essentially of OPG, a variant thereof and/or a fusion protein (or a nucleic acid encoding these molecules) and a pharmaceutically acceptable carrier. In these embodiments, additional therapeutically effective agents are not included in the compositions.

In other embodiments, the pharmaceutical composition includes OPG, a functional fragment, variant, or fusion protein thereof (or a nucleic acid encoding these molecules) and a pharmaceutically acceptable carrier. Addition therapeutic agents, such as agents for the treatment of diabetes, can be included. Thus, the pharmaceutical compositions can include a therapeutically effective amount of another agent. Examples of such agents include, without limitation, anti-apoptotic substances such as the Nemo-Binding Domain and compounds that induce proliferation such as cyclin dependent kinase (CDK)-6, CDK-4 and Cyclin D1. Other active agents can be utilized, such as antidiabetic agents for example, metformin, sulphonylureas (e.g. glibenclamide, tolbutamide, glimepiride), nateglinide, repaglinide, thiazolidinediones (e.g. rosiglitazone, pioglitazone), peroxisome proliferator-activated receptor (PPAR)-gamma-agonists (such as C1262570) and antagonists, PPAR-gamma/alpha modulators (such as KRP 297), alpha-glucosidase inhibitors (e.g. acarbose, voglibose), Dipeptidyl peptidase (DPP)-IV inhibitors (such as LAF237, MK-431), alpha2-antagonists, agents for lowering blood sugar, cholesterol-absorption inhibitors, 3-hydroxy-3-methylglutaryl-coenzyme A (HMG-CoA) reductase inhibitors (such as a statin), insulin and insulin analogues, GLP-1 and GLP-1 analogues (e.g. exendin-4) or amylin. Additional examples inlcude immunomodulatory factors such as anti-CD3 mAb, growth factors such as HGF, VEGF, PDGF, lactogens, and PTHrP.

The pharmaceutically acceptable carriers and excipients useful in this disclosure are conventional. See, e.g., *Remington: The Science and Practice of Pharmacy*, The University of the Sciences in Philadelphia, Editor, Lippincott, Williams, & Wilkins, Philadelphia, Pa., 21$^{st}$ Edition (2005). For instance, parenteral formulations usually comprise injectable fluids that are pharmaceutically and physiologically acceptable fluid vehicles such as water, physiological saline, other balanced salt solutions, aqueous dextrose, glycerol or the like. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate. Excipients that can be included are, for instance, other proteins, such as human serum albumin or plasma preparations.

In some embodiments, OPG, a functional fragment, variant, or fusion protein thereof is included in a controlled release formulation, for example, a microencapsulated formulation. Various types of biodegradable and biocompatible polymers, methods can be used, and methods of encapsulating a variety of synthetic compounds, proteins and nucleic acids, have been well described in the art (see, for example, U.S. Patent Publication Nos. 2007/0148074; 2007/0092575; and 2006/0246139; U.S. Pat. Nos. 4,522,811; 5,753,234; and 7,081,489; PCT Publication No. WO/2006/052285; Benita, *Microencapsulation: Methods and Industrial Applications*, 2$^{nd}$ ed., CRC Press, 2006).

In other embodiments, OPG, a functional fragment, variant, or fusion protein thereof is included in a nanodispersion system. Nanodispersion systems and methods for producing such nanodispersions are well known to one of skill in the art. See, e.g., U.S. Pat. No. 6,780,324; U.S. Pat. Publication No. 2009/0175953. For example, a nanodispersion system includes a biologically active agent and a dispersing agent (such as a polymer, copolymer, or low molecular weight surfactant). Exemplary polymers or copolymers include polyvinylpyrrolidone (PVP), poly(D,L-lactic acid) (PLA), poly(D,L-lactic-co-glycolic acid (PLGA), poly(ethylene glycol). Exemplary low molecular weight surfactants include sodium dodecyl sulfate, hexadecyl pyridinium chloride, polysorbates, sorbitans, poly(oxyethylene) alkyl ethers, poly (oxyethylene) alkyl esters, and combinations thereof. In one example, the nanodispersion system includes PVP and ODP or a variant thereof (such as 80/20 w/w). In some examples, the nanodispersion is prepared using the solvent evaporation method, see for example, Kanaze et al., *Drug Dev. Indus. Pharm.* 36:292-301, 2010; Kanaze et al., *J. Appl. Polymer Sci.* 102:460-471, 2006. With regard to the administration of nucleic acids, one approach to administration of nucleic acids is direct treatment with plasmid DNA, such as with a mammalian expression plasmid. As described above, the nucleotide sequence encoding OPG, a functional fragment, variant, or fusion protein thereof can be placed under the control of a promoter to increase expression of the molecule.

Many types of release delivery systems are available and known to those of ordinary skill in the art. They include polymer based systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems, such as lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which OPG, a functional fragment, variant, or fusion protein thereof, or polynucleotide encoding these polypeptides is contained in a form within a matrix such as those described in U.S. Pat. Nos. 4,452,775; 4,667,014; 4,748,034; 5,239,660; and 6,218,371 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

Use of a long-term sustained release implant may be particularly suitable for treatment of chronic conditions, such as diabetes. Long-term release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. These systems have been described for use with nucleic acids (see U.S. Pat. No. 6,218,371). For use in vivo, nucleic acids and peptides are preferably relatively resistant to degradation (such as via endo- and exo-nucleases). Thus, modifications, such as the inclusion of a C-terminal amide, can be used.

The dosage form of the pharmaceutical composition will be determined by the mode of administration chosen. For instance, in addition to injectable fluids, topical, inhalation, oral and suppository formulations can be employed. Topical preparations can include eye drops, ointments, sprays, patches and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, cellulose, starch, or magnesium stearate. Actual methods of preparing such dosage forms are known, or will be apparent, to those skilled in the art.

The pharmaceutical compositions that include OPG, a functional fragment, variant, or fusion protein thereof can be formulated in unit dosage form, suitable for individual administration of precise dosages. In one specific, non-limiting example, a unit dosage contains from about 1 mg to about 1 g of include OPG, a functional fragment, variant, or fusion protein thereof, such as about 10 mg to about 100 mg, about 50 mg to about 500 mg, about 100 mg to about 900 mg, about 250 mg to about 750 mg, or about 400 mg to about 600 mg. In other examples, a therapeutically effective amount of OPG, a functional fragment, variant, or fusion protein thereof is about 0.01 mg/kg to about 50 mg/kg, for example, about 0.5 mg/kg to about 25 mg/kg or about 1 mg/kg to about 10 mg/kg. In other examples, a therapeutically effective amount of OPG, a functional fragment, variant, or fusion protein thereof is about 1 mg/kg to about 5 mg/kg, for example about 2 mg/kg. In a particular example, a therapeutically effective amount of OPG, a functional fragment, variant, or fusion protein thereof includes about 1 mg/kg to about 10 mg/kg, such as about 2 mg/kg.

The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated. A therapeutically effective amount of OPG, a functional fragment, variant, or fusion protein thereof can be the amount of OPG, a functional fragment, variant, or fusion protein thereof, or a nucleic acid encoding these molecules that is necessary to treat diabetes or affect glucose tolerance.

A therapeutically effective amount can be administered in a single dose, twice daily, weekly, or in several doses, for example daily, or during a course of treatment. However, the therapeutically effective amount will be dependent on the subject being treated, the severity and type of the affliction, and the manner of administration of the therapeutic(s). Islets of β cells can also be treated prior to transplantation into a subject.

When a viral vector is utilized for administration of an nucleic acid encoding OPG, a functional fragment, variant, or fusion protein thereof, it is desirable to provide the recipient with a dosage of each recombinant virus in the composition in the range of from about $10^5$ to about $10^{10}$ plaque forming units/mg mammal, although a lower or higher dose can be administered. The composition of recombinant viral vectors can be introduced into a mammal either prior to any evidence of a cancer, or to mediate regression of the disease in a mammal afflicted with the cancer. Examples of methods for administering the composition into mammals include, but are not limited to, exposure of cells to the recombinant virus ex vivo, or injection of the composition into the affected tissue or intravenous, subcutaneous, intradermal or intramuscular administration of the virus. Alternatively the recombinant viral vector or combination of recombinant viral vectors may be administered locally by direct injection into the cancerous lesion in a pharmaceutically acceptable carrier. Generally, the quantity of recombinant viral vector, carrying the nucleic acid sequence of the polypeptides to be administered is based on the titer of virus particles. An exemplary range to be administered is $10^5$ to $10^{10}$ virus particles per mammal, such as a human.

The compositions of this disclosure that include OPG, a functional fragment, variant, or fusion protein thereof (or nucleic acids encoding these molecules) can be administered to humans or other animals by any means, including orally, intravenously, intramuscularly, intraperitoneally, intranasally, intradermally, intrathecally, subcutaneously, via inhalation or via suppository. In one non-limiting example, the composition is administered orally. In further examples, site-specific administration of the composition can be used, for example by administering OPG, a functional fragment, variant, or fusion protein thereof (or a nucleic acid encoding these molecules) to pancreas tissue (for example by using a pump, or by implantation of a slow release form at the site of the pancreas). As noted above, treatment can involve daily or multi-daily or less than daily (such as weekly or monthly etc.) doses over a period of a few days to months, or even years. In a particular non-limiting example, treatment involves once daily dose or twice daily dose. Islets and/or β cells can be treated prior to transplantation into a subject. The particular mode of administration and the dosage regimen will be selected by the attending clinician, taking into account the particulars of the case (e.g. the subject, the disease, the disease state involved, the particular treatment, and whether the treatment is prophylactic).

The present disclosure also includes combinations of OPG, a functional fragment, variant, or fusion protein thereof, or a nucleic acid encoding one or more of these molecules, with one or more other agents useful in the treatment of diabetes or insulin resistance.

Anti-diabetic agents are generally categorized into six classes: biguanides; thiazolidinediones; sulfonylureas; inhibitors of carbohydrate absorption; fatty acid oxidase inhibitors and anti-lipolytic drugs; and weight-loss agents. Any of these agents can also be used in the methods disclosed herein. The anti-diabetic agents include those agents disclosed in *Diabetes Care,* 22(4):623-634, herein incorporated by reference. One class of anti-diabetic agents of use is the sulfonylureas, which are believed to increase secretion of insulin, decrease hepatic glucogenesis, and increase insulin receptor sensitivity. Another class of anti-diabetic agents of use the biguanide antihyperglycemics, which decrease hepatic glucose production and intestinal absorption, and increase peripheral glucose uptake and utilization, without inducing hyperinsulinemia.

In some examples, OPG, a functional fragment, variant, or fusion protein thereof can be administered in combination with effective doses of anti-diabetic agents (such as biguanides, thiazolidinediones, or incretins) and/or lipid lowering compounds (such as statins or fibrates). The term "administration in combination" or "co-administration" refers to both concurrent and sequential administration of the active agents. Administration of OPG, a functional fragment, variant, or fusion protein thereof or a nucleic acid encoding one or more of these molecules, may also be in combination with lifestyle modifications, such as increased physical activity, low fat diet, low sugar diet, and smoking cessation. Additional agents of use include, without limitation, anti-apoptotic substances such as the Nemo-Binding Domain and compounds that induce proliferation such as cyclin dependent kinase (CDK)-6, CDK-4 and Cyclin D1. Other active agents can be utilized, such as antidiabetic agents for example, metformin, sulphonylureas (e.g. glibenclamide, tolbutamide, glimepiride), nateglinide, repaglinide, thiazolidinediones (e.g. rosiglitazone, pioglitazone), peroxisome proliferator-activated receptor (PPAR)-gamma-agonists (such as C1262570) and antagonists, PPAR-gamma/alpha modulators (such as KRP 297), alpha-glucosidase inhibitors (e.g. acarbose, voglibose), Dipeptidyl peptidase (DPP)-IV inhibitors (such as LAF237, MK-431), alpha2-antagonists, agents for lowering blood sugar, cholesterol-absorption inhibitors, 3-hydroxy-3-methylglutaryl-coenzyme A (HMGCoA) reductase inhibitors (such as a statin), insulin and insulin analogues, GLP-1 and GLP-1 analogues (e.g. exendin-4) or amylin. In some embodiments the agent is an immunomodulatory factor such as anti-CD3 mAb, growth factors such as HGF, vascular endothelial growth factor (VEGF), platelet derived growth factor (PDGF), lactogens, or parathyroid hormone related protein (PTHrP)

It is disclosed herein that of OPG, a functional fragment, variant, or fusion protein thereof increase beta cell survival and proliferation. The beta cell can be a human beta cell. The beta cell can be either in vivo or in vitro. The human beta cells can derived from other cell types such as stem cells (embryonic stem cells, adult stem cells, induced pluripotent stem cells), progenitor cells, or can be produced by transdifferentiation from other cell types Methods of determining or otherwise measuring beta cell proliferation are known in the art. The method can include measuring the number of beta cells in a sample from the subject. The method can also include measuring incorporation of a substance incorporated into DNA, such as, but not limited to, bromodeoxyuridine or Ki-67.

In one embodiment, a membrane permeable cell proliferation dye is utilized. In some examples, the dye is fluorescent. These dyes include, but are not limited to carboxyfluorescein diacetate, or succinimidyl ester. In some examples, a cell proliferation dye is used that is fluorescent and can be identified using fluorescence activated cell sorting. In some embodiments, cell viability is also assayed. There are a variety of suitable cell viability assays which can be used, including, but not limited to, light scattering, viability dye staining, and exclusion dye staining.

In some embodiments, methods are provided for treating diabetes or pre-diabetes in a subject by administering a therapeutically effective amount of a composition including OPG, a functional fragment, variant, or fusion protein thereof, or a nucleic acid encoding one or more of these molecules to the subject. The subject can have diabetes type I or diabetes type II. The subject can be any mammalian subject, including human subjects. The subject can be a child or an adult. The subject can also be administered insulin. The method can include measuring beta cell proliferation.

In some examples, the method includes selecting a subject with diabetes, such as type I or type II diabetes, or a subject at risk for diabetes, such as a subject with pre-diabetes. These subjects can be selected for treatment.

In some examples, a subject with diabetes may be clinically diagnosed by a fasting plasma glucose (FPG) concentration of greater than or equal to 7.0 millimole per liter (mmol/L) (126 milligram per deciliter (mg/dL)), or a plasma glucose concentration of greater than or equal to 11.1 mmol/L (200 mg/dL) at about two hours after an oral glucose tolerance test (OGTT) with a 75 gram (g) load, or in a patient with classic symptoms of hyperglycemia or hyperglycemic crisis, a random plasma glucose concentration of greater than or equal to 11.1 mmol/L (200 mg/dL), or HbA1c levels of greater than or equal to 6.5%. In other examples, a subject with pre-diabetes may be diagnosed by impaired glucose tolerance (IGT). An OGTT two-hour plasma glucose of greater than or equal to 140 mg/dL and less than 200 mg/dL (7.8-11.0 mM), or a fasting plasma glucose (FPG) concentration of greater than or equal to 100 mg/dL and less than 125 mg/dL (5.6-6.9 mmol/L), or HbA1c levels of greater than or equal to 5.7% and less than 6.4% (5.7-6.4%) is considered to be IGT, and indicates that a subject has pre-diabetes. Additional information can be found in *Standards of Medical Care in Diabetes*—2010 (American Diabetes Association, *Diabetes Care* 33:S11-61, 2010, incorporated herein by reference).

In some examples, treating diabetes includes one or more of increasing glucose tolerance, decreasing insulin resistance (for example, decreasing plasma glucose levels, decreasing plasma insulin levels, or a combination thereof), decreasing serum triglycerides, decreasing free fatty acid levels, and decreasing HbA1c levels in the subject. In some embodiments, the disclosed methods include measuring glucose tolerance, insulin resistance, plasma glucose levels, plasma insulin levels, serum triglycerides, free fatty acids, and/or HbA1c levels in a subject.

In some examples, administration of OPG a variant thereof and/or a fusion protein treats diabetes or pre-diabetes by increasing glucose tolerance, for example, by decreasing blood glucose levels (such as two-hour plasma glucose in an OGTT or FPG) in a subject. In some examples, the method includes decreasing blood glucose by at least 5% (such as at least 10%, 15%, 20%, 25%, 30%, 35%, or more) as compared with a control. In particular examples, a decrease in blood glucose level is determined relative to the starting blood glucose level of the subject (for example, prior to treatment with OPG, a functional fragment, variant, or fusion protein thereof). In other examples, decreasing blood glucose levels of a subject includes reduction of blood glucose from a starting point (for example greater than about 126 mg/dL FPG or greater than about 200 mg/dL OGTT two-hour plasma glucose) to a target level (for example, FPG of less than 126 mg/dL or OGTT two-hour plasma glucose of less than 200 mg/dL). In some examples, a target FPG may be less than 100 mg/dL. In other examples, a target OGTT two-hour plasma glucose may be less than 140 mg/dL. Methods to measure blood glucose levels in a subject (for example, in a blood sample from a subject) are routine.

In some embodiments, the disclosed methods include treating a subject with diabetes by increasing beta cell proliferation. In some examples, administration of OPG, a functional fragment, variant, or fusion protein thereof treats diabetes by increasing beta cell number in a subject, for example increasing beta cells proliferation by at least 5% (such as at least 10%, 15%, 20%, 25%, 30%, 35%, 50%, 60%, 70%, 80%, 90%, 100%, 200%, 300% or more) as compared with a control (such as the subject prior to administration of the OPG, variant thereof or fusion thereof). Methods of determining measuring beta cell proliferation are known in the art. The method can include measuring the number of beta cells in a sample, such as a biopsy, from the subject. The method can also include measuring incorporation of a substance incorporated into DNA, such as bromodeoxyuridine or Ki-67.

In other embodiments, the disclosed methods include comparing one or more indicator of diabetes (such as glucose tolerance, triglyceride levels, free fatty acid levels, or HbA1c levels) to a control, wherein an increase or decrease in the particular indicator relative to the control (as discussed above) indicates effective treatment of diabetes. The control can be any suitable control against which to compare the indicator of diabetes in a subject. In some embodiments, the control is a sample obtained from a healthy subject (such as a subject without diabetes). In some embodiments, the control is a historical control or standard reference value or range of values (such as a previously tested control sample, such as a group of subjects with diabetes, or group of samples from subjects that do not have diabetes). In further examples, the control is a reference value, such as a standard value obtained from a population of normal individuals that is used by those of skill in the art. Similar to a control population, the value of the sample from the subject can be compared to the mean reference value or to a range of reference values (such as the high and low values in the reference group or the 95% confidence interval). In other examples, the control is the subject (or group of subjects) treated with placebo compared to the same subject (or group of subjects) treated with the therapeutic compound in a cross-over study. In further examples, the control is the subject (or group of subjects) prior to treatment.

The disclosure is illustrated by the following non-limiting Examples.

EXAMPLES

Example 1

OPG is a Novel Downstream Target of Lactogens in the β Cell

Lactogens play a crucial role in β-cell physiology, with known salutary effects on β-cell growth, function, and survival. Mouse placental lactogen 1 (mPL1) expressed under the rat insulin promoter (RIP) enhances β-cell proliferation, survival and mass in the RIP-mPL1 transgenic (TG) mice. PCR-array analysis in islets from RIP-mPL1 TG and normal (NL) mice have identified OPG as a novel downstream target of lactogens. OPG was the most consistently highly expressed gene in the islets of TG versus NL mice in this analysis (FIG. 2A). These results were confirmed by real-time PCR analysis in TG versus NL islets (FIG. 2B) as well as in INS-1 cells acutely treated with prolactin (Prl, FIG. 2C). Lactogens also increase OPG protein levels in mouse islets (FIG. 2D) and INS-1 cells (FIG. 2E) as seen by Western blot analysis. This is the fourth model of rodent beta cell expansion in which OPG expression is up-regulated, suggesting a correlation between OPG expression and increased beta cell proliferation.

Example 2

Expression of RANK and Death Receptors in Rodent Islets and INS-1 cells

Figure 3A:
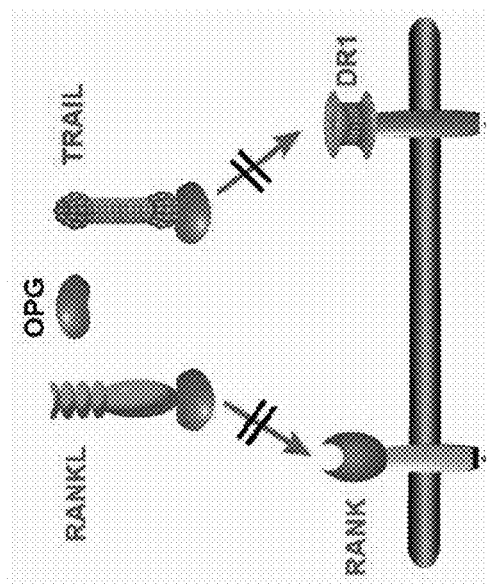
FIGS. 3A-3C are a schematic diagram and a set of bar graphs.
Figure 3B:
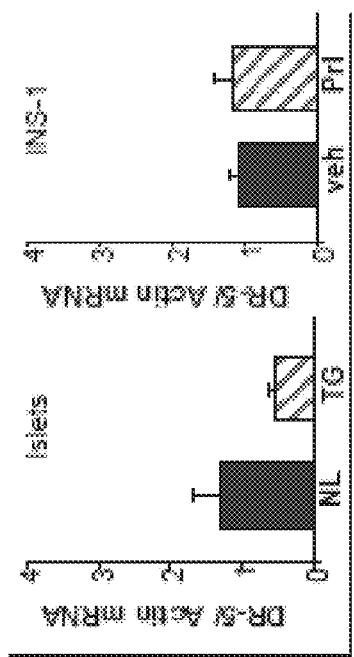
Figure 3C:
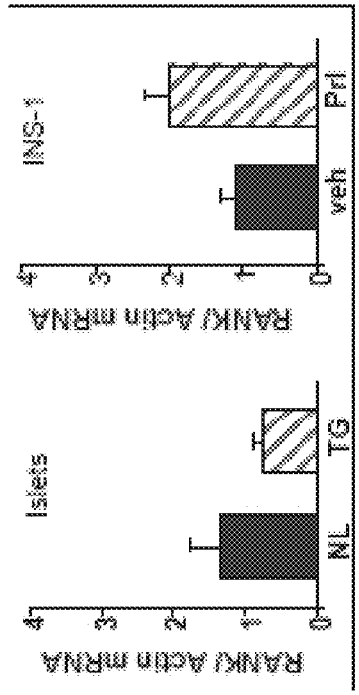

OPG does not have any intrinsic signaling capabilities; it achieves its functions in other cell types through the modulation of two specific ligand/receptor systems, RANKL/RANK and TRAIL/DRs (FIG. 3A). Both ligands, RANKL and TRAIL, are expressed in pancreatic islets. It was examined whether the receptors for these molecules are expressed in rodent islets and in INS-1 cells by real-time PCR using species-specific primers. Results showed that the mRNA of RANK receptor (FIG. 3B) as well as the DR5 receptor (FIG. 3C), (that bind RANKL and TRAIL ligands, respectively) are expressed in mouse islets as well as in INS-1 cells, suggesting that OPG has the potential to act through either pathway in the β-cell.

Example 3

OPG Enhances Rodent β-cell Proliferation In Vivo

Figure 4A:
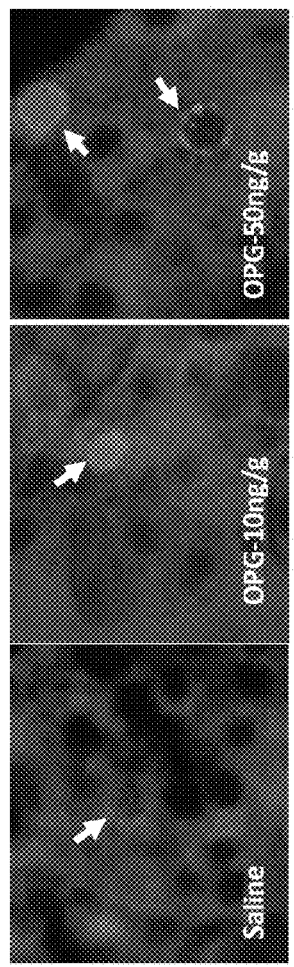
FIGS. 4A-4C show bromodeoxyuridine (BrdU)-positive β-cells in the three groups of mice.

It was hypothesized that OPG will enhance β-cell replication. To test this hypothesis, subcutaneous (s.c.) daily injections of recombinant mouse-Fc chimera OPG (mOPG, R&D Systems) were administered at several different doses (2, 10, 50, 250, 500, 1000, and 2000 ng/g body weight, or saline as control, for 7 days in 8-week old C57BL6 male mice, and measured β-cell proliferation by insulin (green)-bromodeoxyuridine (BrdU) (red) co-staining (FIG. 4A). There was no change in body weight and blood glucose in any of the groups. There was trend to an increase in plasma insulin at higher doses, but it was not statistically significant. An intra peritoneal glucose tolerance test (IPGTT) was performed. All groups were similar to vehicle-treated, although there was a slight improvement in glucose clearance with the higher doses (50-2000 ng). There was no change in beta cell apoptosis in the groups. However, with regard to beta cell proliferation, a 2-3 fold non-significant increase was demonstrated at the lower doses (2-250 ng), and a significant 4-7 fold increase was demonstrated at the higher (500-2000 ng) doses.

A mOPG dose response (0, 10, 50, and 500 ng) study for 30 days in vivo was also performed in 8-week old C57Bl6 mice (n=4 mice/group). Body weight and blood glucose were measured. An IPGTT was performed at 1 and 4 weeks, and an insulin tolerance test (ITT) was performed at 3 weeks. There was no change in these values. Beta cell proliferation was measured at 4 weeks. An increase in beta cell proliferation at 50 and 500 ng doses, which was significant at the 500 ng dose.

Figure 4B:
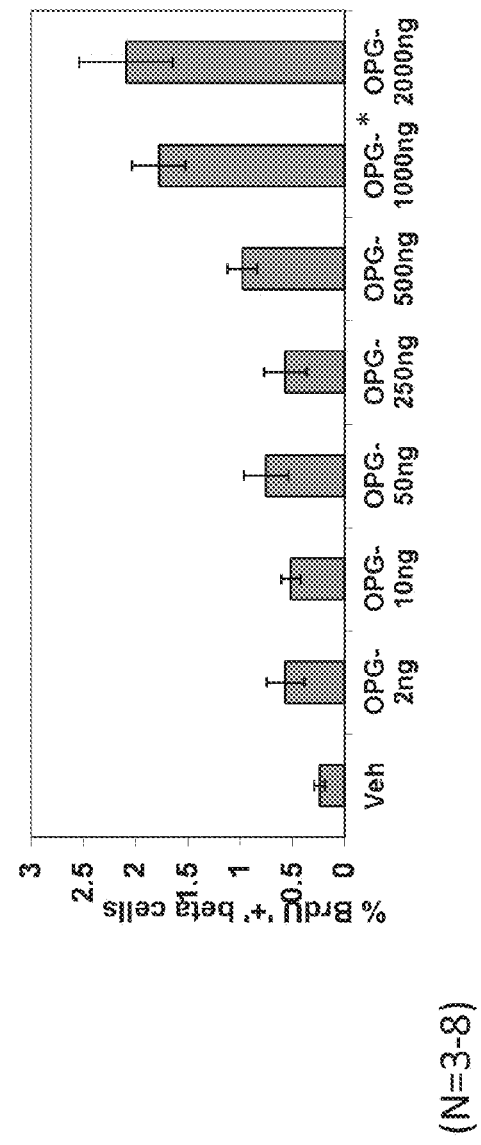
Figure 4C:
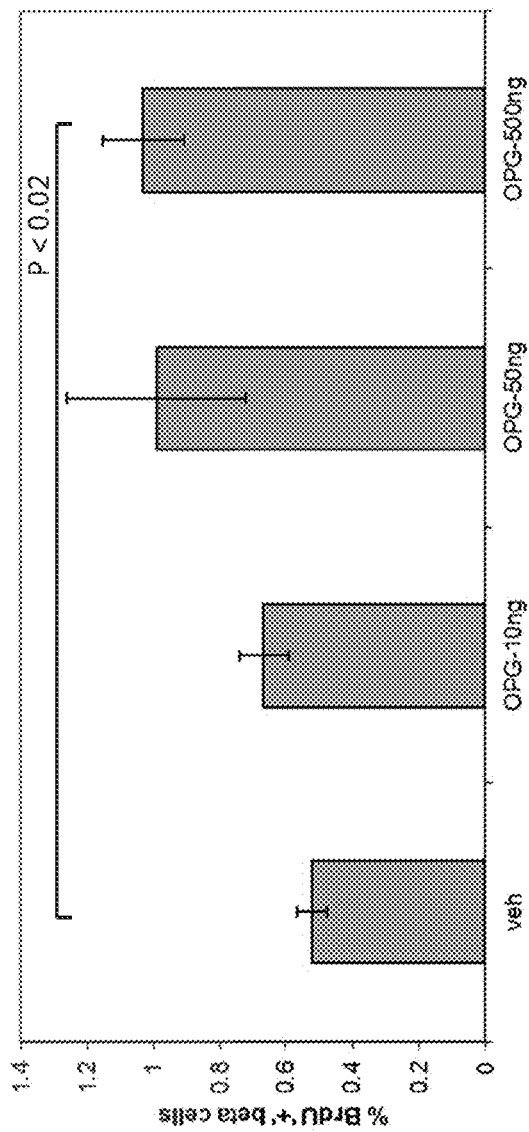

Generally the data showed that at the lower doses (2-250 ng/g) OPG increases beta cell proliferation, although not significantly, by 2-3-fold over control. At the higher doses (500-2000 ng/g) OPG significantly and markedly induces rodent β-cell proliferation by 4-8-fold over control at day 7 in vivo (FIG. 4B) (n=3-8 mice/group). OPG treatment did not negatively affect blood glucose levels nor did it significantly change body weight of these mice. Longer (30 day) treatment with mOPG (10-500 ng/g body weight) also resulted in a significant increase in β-cell proliferation at the higher 500 ng/g dose (FIG. 4C) (n=4-5 mice/group).

Example 4

OPG Induces Human β-cell Replication In Vitro

Figure 5A:
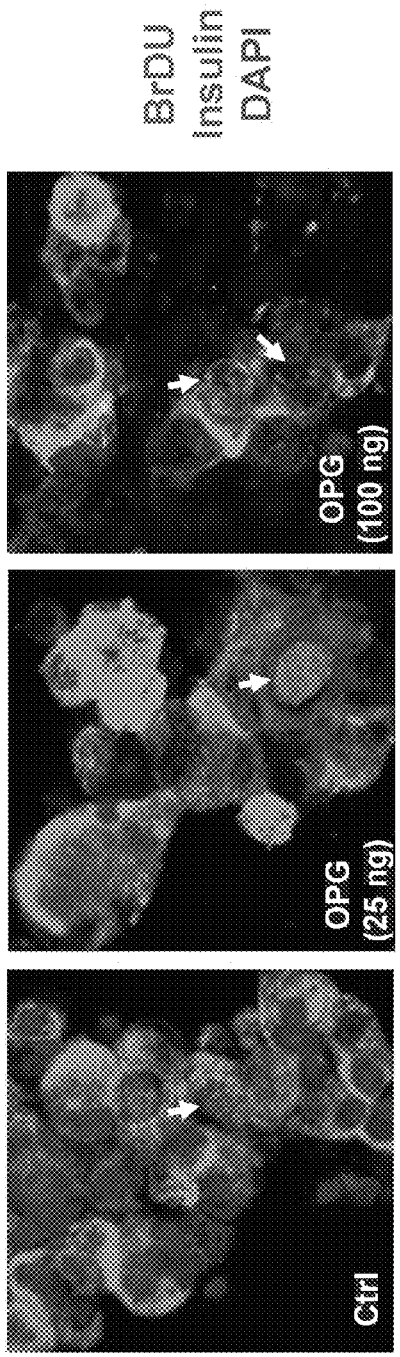
FIGS. 5A-5C shows that OPG enhances human β cell proliferation.
Figure 5C:
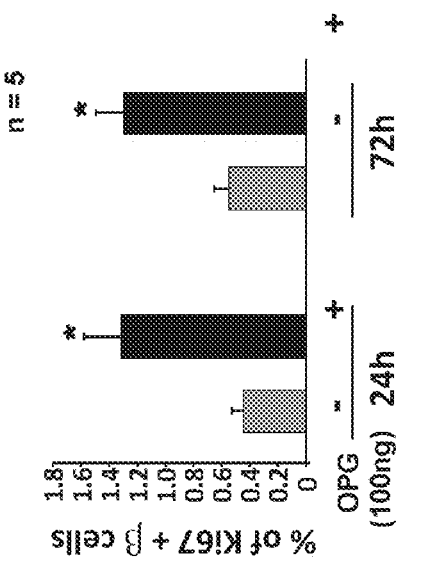
Figure 5B:
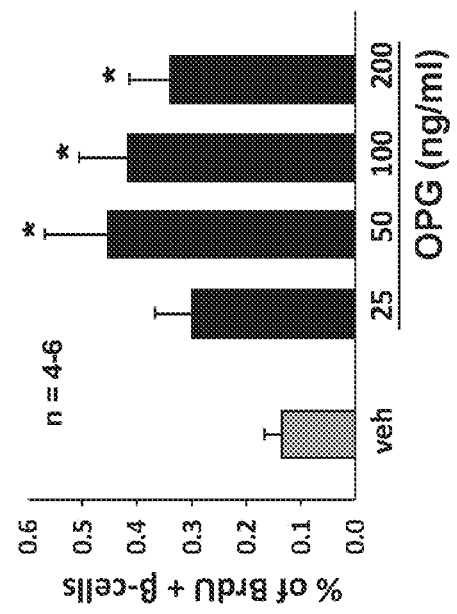

To determine if the in vivo proliferative action of OPG (FIG. 4) is a result of a direct effect on the β-cell, and whether this can be reproduced in human β-cells in vitro, additional studies were performed. Human islet cell cultures were treated with different doses, 25, 50, 100, and 200 ng/ml of recombinant human-Fc chimera OPG (hOPG), or vehicle (veh), for 24 h and quantified β-cell proliferation by BrdU-insulin co-staining (FIG. 5A). There was a significant increase in human β-cell replication with the three higher doses of hOPG (FIG. 5B). Beta cell replication was also measured using a different assay, insulin-Ki67 co-staining, of human islet cell cultures treated with 100 ng/ml of hOPG or vehicle as control for two different time-points, 24 h and 72 h. OPG significantly enhanced human beta cell proliferation at both time points with this method (FIG. 5C). This result also demonstrates that OPG has a proliferative effect in aged β-cells, as the average age of the human islet donors was 50.3±3.3 years.

Example 5

OPG Improves Human β-cell Survival

Figure 6A:
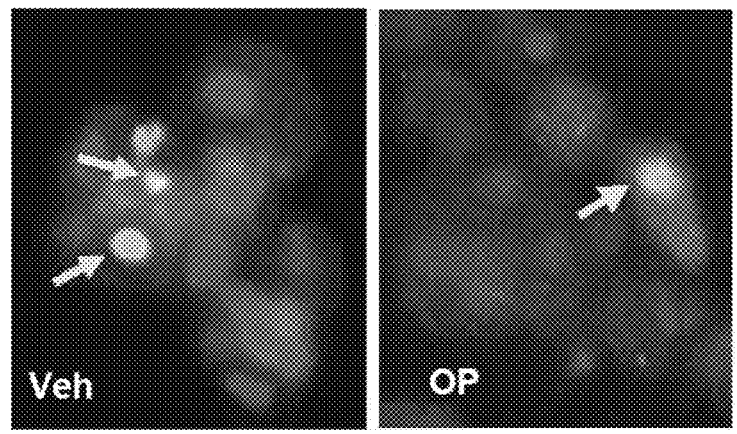
FIGS. 6A-6C (FIG. 6A) Human β-cell death measured by insulin (red), TUNEL (green), and DAPI (blue) co-staining under GLT conditions for 36 h in vehicle (veh) and hOPG (200 ng/ml) treated human islet cell cultures.
Figure 6B:
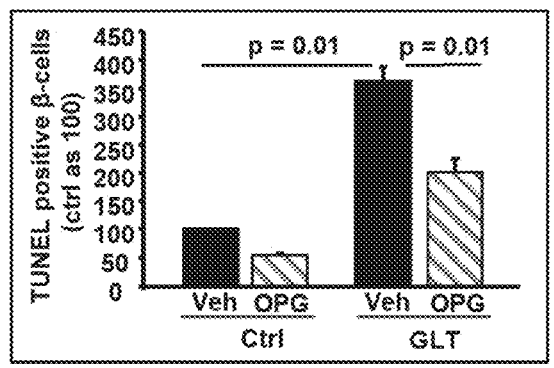
Figure 6C:
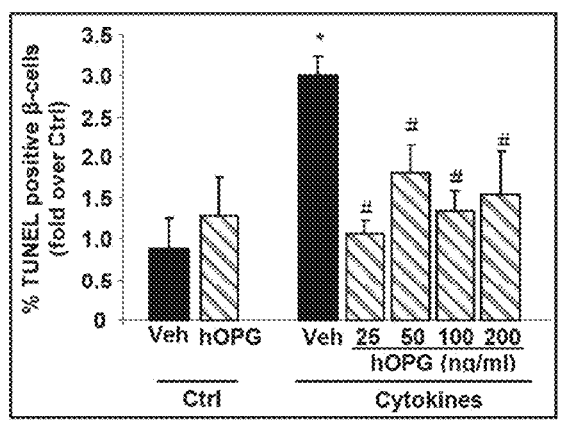

OPG could protect human β-cells against GLT-induced cell death. To examine this, human islet cell cultures were treated with 200 ng/ml of hOPG for 36 h±GLT (25 mM glucose and 0.5 mM palmitate), and β-cell death quantified by TUNEL insulin co-staining (FIG. 6A). Human β-cells were significantly protected against GLT-induced cell death in hOPG-versus vehicle-treated cells (FIG. 6B). It was determined if OPG enhanced survival of human β-cells against cytokine induced cell death. The results indicate that different doses (25-200 ng/ml) of hOPG protect human β-cells against cytokine-induced cell death (FIG. 6C).

The studies disclosed herein identify OPG as a novel, biological downstream target of lactogens in β-cells. Proliferative effects of OPG were observed in human β-cells in vitro. This effect clearly suggests that OPG has regenerative potential to enhance endogenous functional β-cell mass under stress-induced conditions. The pro-survival effects of OPG against cytokines in human islets (FIG. 6C), strongly suggest that OPG treatment will protect/delay the onset of Type 1 diabetes. OPG can be administered repeatedly, such as for months (for example 1-12 months), or years (for example at least 1, 2, 3, 4 or 5 years).

Example 6

Systemic OPG Administration on Rodent Beta Cell Growth, Function, and Survival Under Basal, Aging, Regenerative, and Type 1 Diabetes Conditions The effect of different doses of mouse OPG administration on glucose and β-cell homeostasis in young adult mice is determined. Aging is known to impair basal β-cell proliferation in rodents and in humans. The normal induction in proliferation caused by injury is also impaired in β-cells of older mice. Despite this there have been very few studies that directly address the regenerative therapeutic potential of growth factors on the "aged" β-cell.

OPG can have the capacity to enhance basal β-cell proliferation in older mice. The ability to stimulate β-cell proliferation in human donors with an average age of 50.3±3.3 years, by three different doses of OPG (FIG. 5), suggests that OPG will induce β-cell proliferation in older mice. Regeneration of β-cell mass in patients with diabetes will requires an agent that, when administered acutely, stimulates β-cell hyperplasia in the already injured endocrine pancreas without negatively affecting glucose homeostasis.

The regenerative potential of OPG using double transgenic mice in which the diphtheria toxin (DT) receptor (DTR) is expressed specifically in the β-cell, and cell death is induced upon acute injection of the DT ligand. This model for regeneration, is inducible and reversible.

Different doses of systemic OPG administration on glucose and β-cell homeostasis are tested in young adult mice. Eight week old C57BL6 male mice are injected daily s.c. with mouse recombinant OPG (mOPG, from R & D Systems) at the following doses: 10, 50, 100, 200, 500, and 1000 ng/g body weight, or an equal volume of saline as control. The effects of these doses at two different time points, 7 and 30 days, are examined see FIG. 7.

Figure 7:
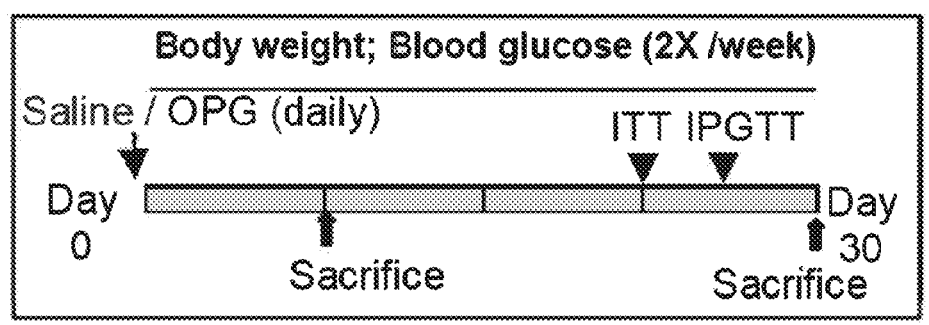
FIG. 7 is a schematic diagram of a treatment protocol.

9-month-old C57BL6 male mice from JAX labs are first aged to 12 months, and then subjected to a similar experimental design, mOPG doses (10-1000 ng/g), and outcome measurements as outlined and FIG. 7.

Figures 8A, 8B:
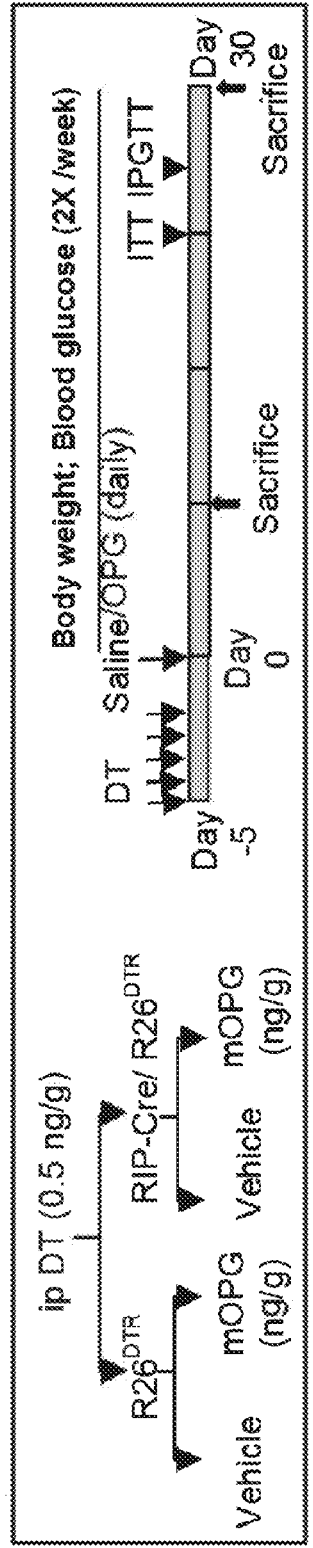
FIGS. 8A-8B Four treatment groups for the mice (FIG. 8A); experimental design (FIG. 8B), depicting time of various treatments. BrdU is injected 6 h before sacrifice at which time pancreas and blood is collected.
Figure 9:
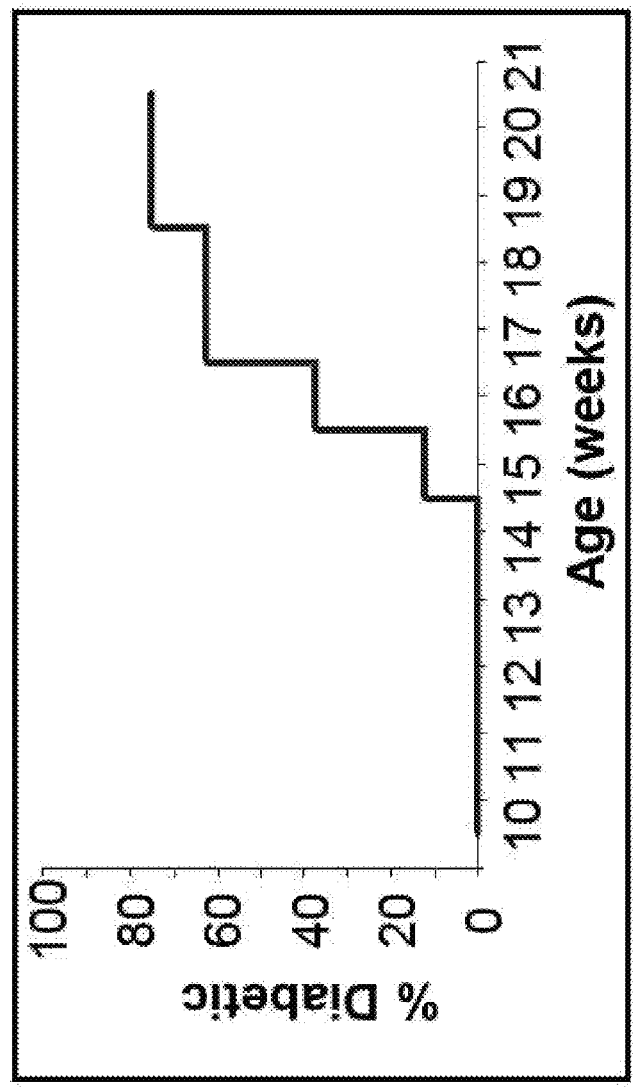
FIG. 9 Percent diabetic NOD/Ltj female mice injected daily with saline, starting at 10-weeks of age with treatment continuing up to 21-weeks of age. Blood glucose was measured weekly, and mice with glucose values >250 mg/dl were considered diabetic (n=8).

The regenerative potential of OPG administration is evaluated in the double transgenic DTR mouse model. This system has been widely used previously (Buch T, et al., Nat Methods 2:419-426, 2005; Criscimanna A, et al. Gastroenterology 141:1451-1462, 2011.) and the two transgenic lines required, R26$^{DTR}$ and the RIP-Cre mice are available in JAX labs. Briefly, RIP-Cre mice are bred with the R26$^{DTR}$ mice to obtain double transgenic hemizygous RIP-Cre/R26$^{DTR}$ mice that expresses DTR in their β-cells due to removal of a floxed stop signal in front of the DTR cDNA. Eight week old male RIP-Cre/R26$^{DTR}$ or control R26$^{DTR}$ mice will be injected intraperitoneally (ip) daily for 5 days with diphtheria toxin (DT) 0.5 ng/g body weight to induce destruction of the DTR-expressing β-cell. After the last DT injection, the mice are treated with vehicle or mOPG and body weight, blood glucose, plasma insulin, IPGTT, and ITT measured on the days indicated in FIG. 8 A,B. Mice are sacrificed at one and four weeks when β-cell parameters including, proliferation, death, and mass will be measured.

To determine the effect of OPG administration on glucose and β-cell homeostasis in NOD/Ltj mice, a model of Type 1 diabetes is utilized. NOD/Ltj female mice, a well characterized model of autoimmune Type 1 diabetes, obtained from JAX labs is used for these studies. 14 week old pre-diabetic NOD/Ltj female mice are injected with saline (as control) or mOPG for 1, 2, and 6 weeks, and glucose and β-cell homeostasis is assessed. It is determined whether OPG treatment delays or prevents the occurrence of diabetes in these mice over the 6-week period. At the 1 and 2 week earlier time points, the rate of β-cell death and insulitis is examined.

Example 7

The Direct Effect of OPG on Human and Rodent Beta Cell Proliferation, Survival, and Function In Vitro To examine the effect of OPG on rodent and human β-cell proliferation in vitro.

The data presented herein shows that different doses of human OPG (hOPG) can induce β-cell proliferation in human islet cell cultures from donors with an average age of 50.3±3.3 years (FIG. 5). The proliferation response at different doses of 0.05-5.0 µg/ml of hOPG and the proliferative response at different times (1-7 days) after treatment is examined, fresh hOPG peptide is added daily to the human islet cell culture. Human β-cell proliferation is measured by insulin-BrdU co-staining, shown in FIG. 5.

To examine the effect of OPG on rodent and human β-cell survival in vitro.

Glucolipotoxicity (GLT), cytokines, and endoplasmic reticular (ER)-stress are causes of β-cell death in diabetes. For additional confirmatory studies, the pro-survival effects of hOPG against these cell death inducers on human β-cells in vitro, is characterization in terms of duration and dose-dependency. The effect of different doses of hOPG, ranging from 0.05-5.0 µg/ml, is tested. Similar to the experimental design in FIG. 6, human islet cell cultures are pre-treated in the absence of serum with hOPG and subsequently cell death is induced either by GLT (25 mM glucose and 0.5 mM palmitate), human cytokines (IL-1β, TNF-α, and IFN-γ), or thapsigargin (0.1-1.0 µM) to induce ER-stress, for 24-96 h, and β-cell death quantified by TUNEL-insulin co-staining. Similar analysis is performed on mouse islets using mouse OPG. GLT and cytokine studies in human islets are done (FIG. 6).

The effect of OPG on rodent and human β-cell function in vitro. The effect of hOPG on insulin expression and glucose-stimulated insulin secretion (GSIS) response in human islets was assessed. Whole human islets treated with vehicle or different concentrations of hOPG (0.05-5.0 µg/ml) for different times (24-96 hrs) were analyzed for insulin expression at the mRNA level by real time PCR, and at the protein level by an RIA for human insulin, and the secretory response assessed by GSIS. OPG did not change GSIS response in human islets.

In certain embodiments, a subject has been determined to have or to be at risk or developing diabetes. For example someone determined to have risk factors (such as obesity) or laboratory evidence (such as an elevated serum glucose or hemoglobin A1c level) of prediabetes or diabetes. The OPG is then administered to the subject for months or years. Laboratory evidence or the condition can be assessed, for example by treating the subject's fasting glucose or HbA1c levels.

Example 8

The Effect of OPG on Human Beta Cells In Vivo

The studies above clearly show that OPG enhances survival and proliferation of human β-cells in vitro (FIGS. 5 and 6). The diabetic non-obese diabetic/severe combined immunodeficient (NOD/SCID) mice, for both mouse and human islets is used to examine the effect of hOPG on human islet transplant outcomes in vivo.

The effect of hOPG in the setting of a suboptimal marginal mass model of human islet transplants in diabetic NOD/SCID mice. NOD/SCID male mice are made diabetic by injection of STZ (2 doses of 125 mg/Kg-body weight given 20 hr apart). Mice with random non-fasted blood glucose >300 mg/dl for three consecutive days are considered diabetic. An insufficient number (1500) of human islet equivalents (IEs, 1 IE=125 μm diameter islet), less than the minimal number of islets required to cause euglycemia, are handpicked and transplanted under the kidney capsule of diabetic immunodeficient NOD/SCID mice, and vehicle or hOPG is administered in the mice from the day of the transplant up to 8 weeks (n=8-10/group). Glucose and β-cell homeostasis, including blood glucose, plasma insulin (mouse and human, using specific RIA kits, IPGTT, β-cell proliferation and death in the islet grafts and in the pancreas are measured at early (1 week) and late (8 weeks) time-points after transplantation. To ensure that euglycemia observed after the transplantation is a result of a functioning human islet graft, transplanted mice undergo unilateral nephrectomy at the end of 8 weeks, and blood glucose is measured daily for the next 7 days. The kidneys with the grafts are stained for insulin to determine the extent of β-cell area present at the graft site 8 weeks after the transplant.

Example 9

Human islet cell cultures (n=3-5) were treated with 25-200 ng of OPG in the presence of bromodeoxyuridine (BrdU) and human beta cell proliferation was assessed by insulin-BrdU co-staining. There was a significant 2.5-3.0 fold increase in human beta cell proliferation with the higher OPG doses. In addition, human islet cell cultures (n=3-5) were treated with 25-200 ng/ml of human recombinant OPG (hOPG) and β-cell proliferation was assessed using Ki-67 co-staining with insulin. There was a significant (3-4-fold) increase in human β-cell proliferation with the higher hOPG doses. This confirmed the observation of the pro-proliferative effect of hOPG on human β-cell proliferation by BrdU staining.

It was examined if OPG had a direct effect on human beta cell survival against glucolipotoxicity (GLT) and cytokines. OPG significantly ameliorated by ~45% and ~50%, the 3.5-fold increase in GLT and cytokine-induced human beta cell death, respectively, as measured by insulin and TUNEL co-staining (n=3), demonstrating a direct pro-survival effect of OPG on human beta cells. These studies reveal OPG to be a novel downstream target of lactogens, which can independently and directly enhance human beta cell proliferation and survival.

It will be apparent that the precise details of the methods or compositions described may be varied or modified without departing from the spirit of the described invention. We claim all such modifications and variations that fall within the scope and spirit of the claims below.

The invention claimed is:

1. A method of increasing proliferation of a human beta cell, comprising
contacting the human beta cell with an effective amount of
(a) a wild type human osteoprotegerin, an osetoprotegerin polypeptide comprising the amino acid sequence set forth as SEQ ID NO: 1, or an osetoprotegerin polypeptide comprising the amino acids 22-401 of the amino acid sequence set forth as SEQ ID NO: 1, or
(b) a fusion protein thereof that binds receptor activator of nuclear factor kappa-B ligand (RANKL),
thereby increasing proliferation of the human beta cell.

2. The method of claim 1, wherein the human beta cell is in vivo.

3. The method of claim 1, wherein the human beta cell is in vitro.

4. The method of claim 1, further comprising measuring proliferation of the human beta cell.

5. The method of claim 1, comprising contacting the beta cell with an effective amount of the osetoprotegerin polypeptide comprising the amino acid sequence set forth as SEQ ID NO: 1 or the osteoprotegerin polypeptide comprising amino acids 22-401 of SEQ ID NO: 1.

6. The method of claim 1, wherein the human beta cell is a human beta cell from an adult subject.

7. The method of claim 6, further comprising measuring proliferation of the human beta cell.

8. The method of claim 7, wherein measuring proliferation of the human beta cell comprises measuring incorporation of bromodeoxyuridine or Ki-67 into genomic DNA of the beta cell and/or progeny of the human beta cell.

9. The method of claim 7, wherein measuring proliferation of the human beta cell comprises measuring incorporation of a membrane permeable cell proliferation dye into the human beta cell and/or progeny of the human beta cell.

10. The method of claim 1, comprising contacting the human beta cell with the fusion protein, wherein the fusion protein comprises an immunoglobulin Fc.

11. The method of claim 1, comprising contacting the human beta cell with the wild-type human oteoprotegerin.

12. The method of claim 1, comprising contacting the human beta cell with the fusion protein.

13. A method of increasing survival of a human beta cell, comprising
contacting the human beta cell with an effective amount of
a) a wild-type human osteoprotegerin polypeptide, an osteoprotegerin polypeptide comprising the amino acid sequence set forth as SEQ ID NO: 1 or an osteoprotegerin polypeptide comprising amino acids 22-401 of the amino sequence set forth as SEQ ID NO: 1, or
b) a fusion protein thereof that-binds receptor activator of nuclear factor kappa-B ligand (RANKL),
thereby increasing survival of the human beta cell.

14. The method of claim 13, wherein the human beta cell is in vivo.

15. The method of claim 13, wherein the human beta cell is in vitro.

16. The method of claim 13, further comprising measuring survival of the human beta cell.

17. The method of claim 13, comprising contacting the beta cell with the effective amount of the wild-type human osteoprotegerin or the osteoprotegerin polypeptide comprising the amino acid sequence set forth as SEQ ID NO: 1.

18. The method of claim 13, wherein the human beta cell is a human beta cell of an adult subject.

19. The method of claim 13, comprising contacting the human beta cell with the fusion protein, wherein the fusion protein comprises an immunoglobulin Fc.

20. The method of claim 13, comprising contacting the human beta cell with the oteoprotegerin polypeptide comprising amino acids 22 to 401 of the amino acid sequence set forth as SEQ ID NO: 1.

21. The method of claim 13, comprising contacting the human beta cell with the fusion protein.

* * * * *

SEQUENCE LISTING

```
<160> NUMBER OF SEQ ID NOS: 2

<210> SEQ ID NO 1
<211> LENGTH: 401
<212> TYPE: PRT
<213> ORGANISM: Homo sapiens

<400> SEQUENCE: 1

Met Asn Lys Leu Leu Cys Cys Ala Leu Val Phe Leu Asp Ile Ser Ile
1               5                   10                  15

Lys Trp Thr Thr Gln Glu Thr Phe Pro Pro Lys Tyr Leu His Tyr Asp
            20                  25                  30

Glu Glu Thr Ser His Gln Leu Leu Cys Asp Lys Cys Pro Pro Gly Thr
        35                  40                  45

Tyr Leu Lys Gln His Cys Thr Ala Lys Trp Lys Thr Val Cys Ala Pro
    50                  55                  60

Cys Pro Asp His Tyr Tyr Thr Asp Ser Trp His Thr Ser Asp Glu Cys
65                  70                  75                  80

Leu Tyr Cys Ser Pro Val Cys Lys Glu Leu Gln Tyr Val Lys Gln Glu
                85                  90                  95

Cys Asn Arg Thr His Asn Arg Val Cys Glu Cys Lys Glu Gly Arg Tyr
            100                 105                 110

Leu Glu Ile Glu Phe Cys Leu Lys His Arg Ser Cys Pro Pro Gly Phe
        115                 120                 125

Gly Val Val Gln Ala Gly Thr Pro Glu Arg Asn Thr Val Cys Lys Arg
    130                 135                 140
```

Cys Pro Asp Gly Phe Phe Ser Asn Glu Thr Ser Ser Lys Ala Pro Cys
145                 150                 155                 160

Arg Lys His Thr Asn Cys Ser Val Phe Gly Leu Leu Leu Thr Gln Lys
            165                 170                 175

Gly Asn Ala Thr His Asp Asn Ile Cys Ser Gly Asn Ser Glu Ser Thr
            180                 185                 190

Gln Lys Cys Gly Ile Asp Val Thr Leu Cys Glu Glu Ala Phe Phe Arg
        195                 200                 205

Phe Ala Val Pro Thr Lys Phe Thr Pro Asn Trp Leu Ser Val Leu Val
210                 215                 220

Asp Asn Leu Pro Gly Thr Lys Val Asn Ala Glu Ser Val Glu Arg Ile
225                 230                 235                 240

Lys Arg Gln His Ser Ser Gln Glu Gln Thr Phe Gln Leu Leu Lys Leu
                245                 250                 255

Trp Lys His Gln Asn Lys Ala Gln Asp Ile Val Lys Ile Ile Gln
            260                 265                 270

Asp Ile Asp Leu Cys Glu Asn Ser Val Gln Arg His Ile Gly His Ala
        275                 280                 285

Asn Leu Thr Phe Glu Gln Leu Arg Ser Leu Met Glu Ser Leu Pro Gly
290                 295                 300

Lys Val Gly Ala Glu Asp Ile Glu Lys Thr Ile Lys Ala Cys Lys
305                 310                 315                 320

Pro Ser Asp Gln Ile Leu Lys Leu Leu Ser Leu Trp Arg Ile Lys Asn
                325                 330                 335

Gly Asp Gln Asp Thr Leu Lys Gly Leu Met His Ala Leu Lys His Ser
            340                 345                 350

Lys Thr Tyr His Phe Pro Lys Thr Val Thr Gln Ser Leu Lys Lys Thr
        355                 360                 365

Ile Arg Phe Leu His Ser Phe Thr Met Tyr Lys Leu Tyr Gln Lys Leu
370                 375                 380

Phe Leu Glu Met Ile Gly Asn Gln Val Gln Ser Val Lys Ile Ser Cys
385                 390                 395                 400

Leu

<210> SEQ ID NO 2
<211> LENGTH: 1346
<212> TYPE: DNA
<213> ORGANISM: Homo sapiens

<400> SEQUENCE: 2
gtatatataa cgtgatgagc gtacgggtgc ggagacgcac cggagcgctc gcccagccgc    60
cgyctccaag cccctgaggt tccggggac cacaatgaac aagttgctgt gctgcgcgct   120
gacatctcca ttaagtggac cacccaggaa acgtttcctc caaagtacct tcattatgac   180
gaagaaacct ctcatcagct gttgtgtgac aaatgtcctc ctggtaccta cctaaaacaa   240
cactgtacag caaagtggaa gaccgtgtgc gcccttgcc ctgaccacta ctacacagac   300
agctggcaca ccagtgacga gtgtctatac tgcagccccg tgtgcaagga gctgcagtac   360
gtcaagcagg agtgcaatcg cacccacaac cgcgtgtgcg aatgcaagga agggcgctac   420
cttgagatag agttctgctt gaaacatagg agctgccctc ctggatttgg agtggtgcaa   480
gctggaaccc cagagcgaaa tacagtttgc aaaagatgtc cagatgggtt cttctcaaat   540
gagacgtcat ctaaagcacc ctgtagaaaa cacacaaatt gcagtgtctt ggtctcctg   600 ctaactcaga aaggaaatgc aacacacgac aacatatgtt ccggaaacag tgaatcaact   660

```
caaaaatgtg gaatagatgt taccctgtgt gaggaggcat tcttcaggtt tgctgttcct    720
acaaagttta cgcctaactg gcttagtgtc ttggtagaca atttgcctgg caccaaagta    780
aacgcagaga gtgtagagag gataaaacgg caacacagct cacaagaaca gactttccag    840
ctgctgaagt tatggaaaca tcaaaacaaa gcccaagata tagtcaagaa gatcatccaa    900
gatattgacc tctgtgaaaa cagcgtgcag cggcacattg gacatgctaa cctcaccttc    960
gagcagcttc gtagcttgat ggaaagctta ccgggaaaga aagtgggagc agaagacatt   1020
gaaaaaacaa taaaggcatg caaacccagt gaccagatcc tgaagctgct cagtttgtgg   1080
cgaataaaaa atggcgacca agacaccttg aagggcctaa tgcacgcact aaagcactca   1140
aagacgtacc actttcccaa aactgtcact cagagtctaa agaagaccat caggttcctt   1200
cacagcttca caatgtacaa attgtatcag aagttattt tagaaatgat aggtaaccag    1260
gtccaatcag taaaaataag ctgcttataa ctggaaatgg ccattgagct gtttcctcac   1320
aattggcgag atcccatgga tgataa                                        1346
```